(12) United States Patent
Small

(10) Patent No.: US 7,902,415 B2
(45) Date of Patent: Mar. 8, 2011

(54) PROCESSES FOR DIMERIZING OR ISOMERIZING OLEFINS

(75) Inventor: Brooke L. Small, Kingwood, TX (US)

(73) Assignee: Chevron Phillips Chemical Company LP, The Woodlands, TX (US)

(*) Notice: Subject to any disclaimer, the term of this patent is extended or adjusted under 35 U.S.C. 154(b) by 492 days.

(21) Appl. No.: 11/963,252

(22) Filed: Dec. 21, 2007

(65) Prior Publication Data

US 2009/0163755 A1 Jun. 25, 2009

(51) Int. Cl.
*C07C 2/24* (2006.01)

(52) U.S. Cl. ......... 585/513; 585/502; 585/510; 585/511; 585/512; 585/520; 585/521; 585/523

(58) Field of Classification Search .................. 585/510, 585/511, 512, 513, 502, 520, 521, 523
See application file for complete search history.

(56) References Cited

U.S. PATENT DOCUMENTS

| | | |
|---|---|---|
| 3,635,869 A | 1/1972 | Steele et al. |
| 3,819,746 A | 6/1974 | Katzakian, Jr. et al. |
| 3,873,602 A | 3/1975 | Katzakian, Jr. et al. |
| 3,932,285 A | 1/1976 | Ceprini et al. |
| 3,962,182 A | 6/1976 | Steele et al. |
| 3,968,135 A | 7/1976 | Steele et al. |
| 3,977,996 A | 8/1976 | Katzakian, Jr. et al. |
| 3,978,026 A | 8/1976 | Katzakian, Jr. et al. |
| 4,017,429 A | 4/1977 | Steele et al. |
| 4,057,565 A | 11/1977 | Manzer |
| 4,451,573 A | 5/1984 | Ikegami et al. |
| 4,668,838 A | 5/1987 | Briggs |
| 4,777,315 A | 10/1988 | Levine et al. |
| 4,853,356 A | 8/1989 | Briggs |
| 4,876,229 A | 10/1989 | Furtek |
| 4,971,986 A | 11/1990 | Stanek et al. |
| 5,081,089 A | 1/1992 | Rekers et al. |
| 5,118,648 A | 6/1992 | Furtek et al. |
| 5,137,994 A | 8/1992 | Goode et al. |
| 5,198,401 A | 3/1993 | Turner et al. |
| 5,198,563 A | 3/1993 | Reagen et al. |
| 5,288,823 A | 2/1994 | Reagan et al. |
| 5,331,070 A | 7/1994 | Pettijohn et al. |
| 5,331,104 A | 7/1994 | Reagen et al. |
| 5,340,785 A | 8/1994 | Reagen et al. |
| 5,340,892 A | 8/1994 | Kuramoto |
| 5,360,879 A | 11/1994 | Reagen et al. |
| 5,376,612 A | 12/1994 | Reagen et al. |
| 5,382,738 A | 1/1995 | Reagen et al. |
| 5,393,719 A | 2/1995 | Pettijohn et al. |
| 5,399,539 A | 3/1995 | Reagen et al. |
| 5,438,027 A | 8/1995 | Reagen et al. |
| 5,451,645 A | 9/1995 | Reagen et al. |
| 5,470,926 A | 11/1995 | Reagen et al. |
| 5,491,272 A | 2/1996 | Tanaka et al. |
| 5,523,507 A | 6/1996 | Reagen et al. |
| 5,543,375 A | 8/1996 | Lashier et al. |
| 5,550,305 A | 8/1996 | Wu |
| 5,557,026 A | 9/1996 | Tanaka et al. |
| 5,563,312 A | 10/1996 | Knudsen et al. |
| 5,689,028 A | 11/1997 | Lashier et al. |
| 5,696,240 A | 12/1997 | Vallarino et al. |
| 5,714,556 A | 2/1998 | Johnson et al. |
| 5,731,487 A | 3/1998 | Tamura et al. |
| 5,744,677 A | 4/1998 | Wu |
| 5,750,816 A | 5/1998 | Araki et al. |
| 5,750,817 A | 5/1998 | Tanaka et al. |
| 5,763,723 A | 6/1998 | Reagen et al. |
| 5,786,291 A | 7/1998 | Speca et al. |
| 5,786,431 A | 7/1998 | Reagen et al. |
| 5,811,618 A | 9/1998 | Wu |
| 5,814,575 A | 9/1998 | Reagen et al. |
| 5,830,955 A | 11/1998 | Takeda et al. |
| 5,856,257 A | 1/1999 | Freeman et al. |

(Continued)

FOREIGN PATENT DOCUMENTS

AU 650808 6/1994

(Continued)

OTHER PUBLICATIONS

Small, et al "Iron Catalysts for the Head-to-Head Dimerization of α-Olefins and Mechanistic Implications for the Production of Linear α-Olefins," Organometallics, 2001, 20, 5738-5744.*
Small, et al "Iron Catalysts for the Head-to-Head Dimerization of α-Olefins and Mechanistic Implications for the Production of Linear α-Olefins," Organometallics, 2001, 20, 5738-5744.*
Adams, Harry, et al., "Complexes of ligands providing endogenous bridges. Part 1. The syntheses and crystal structures of barium and lead(II) complexes of macrocyclic schiff bases derived from heterocyclic dicarbonyls and 1,n-diamino-n'-hydroxyalkanes (n,n' = 3,2; 4,2; or 5,3)," XP009070491, 1987, pp. 207-218, J. Chem. Soc. Dalton Trans.
Advisory Action dated Aug. 9, 2006 (3 pages), U.S. Appl. No. 10/783,429, filed Feb. 20, 2004.
Advisory Action dated Mar. 29, 2007 (3 pages), U.S. Appl. No. 10/783,429, filed Feb. 20, 2004.
Allen, Geoffrey, Editor, "Comprehensive polymer science, vol. 4," 1989, pp. 1-108, 409-412, 533-584 plus 1 cover page, 2 publishing pages, and 2 contents pages, Pergamon Press, England.

(Continued)

*Primary Examiner* — Glenn A Caldarola
*Assistant Examiner* — Bradley Etherton
(74) *Attorney, Agent, or Firm* — Conley Rose, P.C.; Rodney B. Carroll; Lynda S. Jolly

(57) ABSTRACT

A process for dimerizing alpha olefins comprising contacting (i) an alpha olefin having at least 3 carbon atoms, (ii) a hexadentate bimetallic catalyst, and (iii) a cocatalyst, and dimerizing the alpha olefin in a reaction zone at conditions effective to dimerize an alpha olefin to form a reaction zone effluent comprising alpha olefin oligomers including alpha olefin dimers. A process for dimerizing olefins comprising contacting (i) an alpha olefin having at least 3 carbon atoms, (ii) a hexadentate bimetallic complex comprising a cobalt compound, and (iii) a cocatalyst, and dimerizing the alpha olefin in a reaction zone at conditions effective to dimerize an alpha olefin to form a reaction zone effluent comprising oligomers including dimmers, wherein greater than 20 weight percent of the alpha olefin has been converted to oligomers, greater than 30 weight percent of the oligomers are dimers, and greater than 85 mole percent of the dimers are linear.

26 Claims, No Drawings

U.S. PATENT DOCUMENTS

| | | | |
|---|---|---|---|
| 5,856,610 A | 1/1999 | Tamura et al. | |
| 5,856,612 A | 1/1999 | Araki et al. | |
| 5,859,303 A | 1/1999 | Lashier | |
| 5,910,619 A | 6/1999 | Urata et al. | |
| 5,919,996 A | 7/1999 | Freeman et al. | |
| 5,955,555 A | 9/1999 | Bennett | |
| 5,968,866 A | 10/1999 | Wu | |
| 5,986,153 A | 11/1999 | Kallenbach et al. | |
| 6,031,145 A | 2/2000 | Commereuc et al. | |
| 6,063,881 A * | 5/2000 | Bennett | 526/161 |
| 6,103,654 A | 8/2000 | Commereuc et al. | |
| 6,103,658 A | 8/2000 | Mackenzie et al. | |
| 6,103,946 A | 8/2000 | Brookhart, III et al. | |
| 6,127,301 A | 10/2000 | Iwanaga et al. | |
| 6,133,495 A | 10/2000 | Urata et al. | |
| 6,150,482 A | 11/2000 | Brookhart et al. | |
| 6,214,761 B1 | 4/2001 | Bennett | |
| 6,221,986 B1 | 4/2001 | Commereuc et al. | |
| 6,239,237 B1 | 5/2001 | Xu et al. | |
| 6,281,303 B1 | 8/2001 | Lavoie et al. | |
| 6,291,733 B1 | 9/2001 | Small et al. | |
| 6,337,297 B1 | 1/2002 | Mimura et al. | |
| 6,344,594 B1 | 2/2002 | Sen et al. | |
| 6,369,177 B1 | 4/2002 | Tohi et al. | |
| 6,380,451 B1 | 4/2002 | Kreischer et al. | |
| 6,414,098 B1 | 7/2002 | Engehausen et al. | |
| 6,417,305 B2 | 7/2002 | Bennett | |
| 6,417,364 B1 | 7/2002 | Lenges | |
| 6,423,848 B2 | 7/2002 | Bennett | |
| 6,451,939 B1 | 9/2002 | Britovsek et al. | |
| 6,455,648 B1 | 9/2002 | Freeman et al. | |
| 6,458,739 B1 | 10/2002 | Kimberley et al. | |
| 6,458,905 B1 | 10/2002 | Schmidt et al. | |
| 6,461,994 B1 | 10/2002 | Gibson et al. | |
| 6,465,386 B1 | 10/2002 | Maddox et al. | |
| 6,489,497 B1 | 12/2002 | Brookhart, III et al. | |
| 6,521,806 B1 | 2/2003 | Tamura et al. | |
| 6,534,691 B2 | 3/2003 | Culver et al. | |
| 6,545,108 B1 | 4/2003 | Moody et al. | |
| 6,548,672 B1 | 4/2003 | Gibson et al. | |
| 6,555,633 B1 | 4/2003 | Tanaka et al. | |
| 6,555,723 B2 | 4/2003 | Schiffino | |
| 6,562,973 B1 | 5/2003 | Liu | |
| 6,683,187 B2 | 1/2004 | De Boer et al. | |
| 6,689,848 B2 | 2/2004 | Nagy et al. | |
| 6,710,006 B2 | 3/2004 | De Boer et al. | |
| 6,740,715 B2 | 5/2004 | Brookhart, III et al. | |
| 6,777,584 B2 | 8/2004 | Patil et al. | |
| 6,828,269 B2 | 12/2004 | Commereuc et al. | |
| 6,841,693 B1 * | 1/2005 | Watanabe et al. | 556/32 |
| 6,844,290 B1 | 1/2005 | Maas et al. | |
| 6,900,152 B2 | 5/2005 | Yoshida et al. | |
| 6,903,042 B2 | 6/2005 | Drochon et al. | |
| 6,911,505 B2 | 6/2005 | Small | |
| 6,911,506 B2 | 6/2005 | Small et al. | |
| 6,927,313 B2 | 8/2005 | Bianchini et al. | |
| 7,001,964 B2 * | 2/2006 | Small | 526/348 |
| 7,037,988 B2 | 5/2006 | De Boer et al. | |
| 7,045,632 B2 * | 5/2006 | Small | 546/264 |
| 7,049,442 B2 | 5/2006 | De Boer et al. | |
| 7,053,259 B2 | 5/2006 | Culver et al. | |
| 7,129,304 B1 | 10/2006 | Small et al. | |
| 7,176,266 B2 | 2/2007 | Sato et al. | |
| 7,179,871 B2 | 2/2007 | De Boer et al. | |
| 7,223,893 B2 | 5/2007 | Small et al. | |
| 7,238,764 B2 | 7/2007 | De Boer et al. | |
| 7,268,096 B2 | 9/2007 | Small et al. | |
| 7,271,121 B2 | 9/2007 | Small et al. | |
| 7,297,806 B2 | 11/2007 | Brookhart, III et al. | |
| 7,304,159 B2 | 12/2007 | De Boer et al. | |
| 7,384,886 B2 | 6/2008 | Knudsen et al. | |
| 7,442,819 B2 | 10/2008 | Ionkin et al. | |
| 7,456,284 B2 | 11/2008 | Small | |
| 7,589,245 B2 | 9/2009 | De Boer et al. | |
| 2001/0053742 A1 | 12/2001 | Knudsen et al. | |
| 2004/0116758 A1 | 6/2004 | De Boer et al. | |
| 2004/0122269 A1 | 6/2004 | Van Zon et al. | |
| 2004/0122271 A1 | 6/2004 | Van Zon et al. | |
| 2004/0180778 A1 * | 9/2004 | Small | 502/150 |
| 2005/0187098 A1 | 8/2005 | Knudsen et al. | |
| 2005/0187418 A1 * | 8/2005 | Small et al. | 585/521 |
| 2007/0043181 A1 | 2/2007 | Knudsen et al. | |
| 2007/0112150 A1 | 5/2007 | Small et al. | |
| 2008/0058534 A1 | 3/2008 | Knudsen et al. | |
| 2008/0177122 A1 | 7/2008 | Knudsen et al. | |
| 2009/0270567 A1 | 10/2009 | Small et al. | |

FOREIGN PATENT DOCUMENTS

| | | |
|---|---|---|
| CA | 2087578 A1 | 7/1994 |
| CA | 2396614 A1 | 7/2001 |
| CA | 2115639 C | 10/2004 |
| CN | 1256968 A | 6/2000 |
| CN | 1294109 A | 5/2001 |
| CN | 1306014 A | 8/2001 |
| CN | 1358772 A | 7/2002 |
| CN | 1361093 A | 7/2002 |
| CN | 1374281 A | 10/2002 |
| CN | 1850339 A | 10/2006 |
| EP | 0416815 A2 | 3/1991 |
| EP | 0537609 A2 | 4/1993 |
| EP | 0608447 A1 | 8/1994 |
| EP | 0668105 A2 | 8/1995 |
| EP | 1110930 A1 | 6/2001 |
| EP | 1188762 A1 | 3/2002 |
| EP | 1229020 A1 | 8/2002 |
| EP | 1325924 A1 | 7/2003 |
| FR | 2833191 A1 | 6/2003 |
| FR | 2857964 A1 | 1/2005 |
| JP | 6263822 | 9/1994 |
| JP | 7010780 | 1/1995 |
| JP | 7017878 | 1/1995 |
| JP | 7018013 | 1/1995 |
| JP | 7118173 | 5/1995 |
| JP | 7118174 | 5/1995 |
| JP | 7118175 | 5/1995 |
| JP | 7118324 | 5/1995 |
| JP | 7118325 | 5/1995 |
| JP | 7118326 | 5/1995 |
| JP | 7118327 | 5/1995 |
| JP | 7118328 | 5/1995 |
| JP | 7149671 | 6/1995 |
| JP | 7149672 | 6/1995 |
| JP | 7149673 | 6/1995 |
| JP | 7149674 | 6/1995 |
| JP | 7149675 | 6/1995 |
| JP | 7149676 | 6/1995 |
| JP | 7149677 | 6/1995 |
| JP | 7157512 | 6/1995 |
| JP | 7215896 | 8/1995 |
| JP | 8059732 | 3/1996 |
| JP | 8134131 | 5/1996 |
| JP | 8151409 | 6/1996 |
| JP | 8183747 | 7/1996 |
| JP | 8239330 | 9/1996 |
| JP | 8239331 | 9/1996 |
| JP | 8239418 | 9/1996 |
| JP | 8245429 | 9/1996 |
| JP | 8245430 | 9/1996 |
| JP | 8245431 | 9/1996 |
| JP | 8283330 | 10/1996 |
| JP | 8283332 | 10/1996 |
| JP | 8301921 | 11/1996 |
| JP | 8301922 | 11/1996 |
| JP | 8301923 | 11/1996 |
| JP | 8301924 | 11/1996 |
| JP | 8301925 | 11/1996 |
| JP | 8325317 | 12/1996 |
| JP | 8325318 | 12/1996 |
| JP | 8325319 | 12/1996 |
| JP | 8333407 | 12/1996 |
| JP | 9012627 | 1/1997 |
| JP | 9020692 | 1/1997 |
| JP | 9020693 | 1/1997 |
| JP | 9040710 | 2/1997 |
| JP | 9087318 | 3/1997 |
| JP | 9143213 | 6/1997 |
| JP | 9176228 | 7/1997 |

| | | |
|---|---|---|
| JP | 9176229 | 7/1997 |
| JP | 9188634 | 7/1997 |
| JP | 9194400 | 7/1997 |
| JP | 9194524 | 7/1997 |
| JP | 9262480 | 10/1997 |
| JP | 9268133 | 10/1997 |
| JP | 9268134 | 10/1997 |
| JP | 9268135 | 10/1997 |
| JP | 10007593 | 1/1998 |
| JP | 10007594 | 1/1998 |
| JP | 10007595 | 1/1998 |
| JP | 10007681 | 1/1998 |
| JP | 10036431 | 2/1998 |
| JP | 10036432 | 2/1998 |
| JP | 10036433 | 2/1998 |
| JP | 10036435 | 2/1998 |
| JP | 10045634 | 2/1998 |
| JP | 10045638 | 2/1998 |
| JP | 10045833 | 2/1998 |
| JP | 10060043 | 3/1998 |
| JP | 10087517 | 4/1998 |
| JP | 10087518 | 4/1998 |
| JP | 10101587 | 4/1998 |
| JP | 10218799 | 8/1998 |
| JP | 11060511 | 3/1999 |
| JP | 11060626 | 3/1999 |
| JP | 11092407 | 4/1999 |
| JP | 11092408 | 4/1999 |
| JP | 2000176291 | 6/2000 |
| JP | 2000202299 | 7/2000 |
| JP | 2000212212 | 8/2000 |
| JP | 2001002724 | 1/2001 |
| JP | 2001009290 | 1/2001 |
| JP | 2001096164 | 4/2001 |
| JP | 2001149788 | 6/2001 |
| JP | 2001187345 | 7/2001 |
| JP | 2002045703 | 2/2002 |
| JP | 2002066329 | 3/2002 |
| JP | 2002102710 | 4/2002 |
| JP | 2002172327 | 6/2002 |
| JP | 2002200429 | 7/2002 |
| JP | 2002205960 | 7/2002 |
| JP | 2002233764 | 8/2002 |
| JP | 2002233765 | 8/2002 |
| JP | 2003071294 | 3/2003 |
| JP | 2003088760 | 3/2003 |
| JP | 2004136270 | 5/2004 |
| JP | 2004136271 | 5/2004 |
| JP | 2004306014 | 11/2004 |
| KR | 20030029253 | 4/2003 |
| WO | 9415940 A1 | 7/1994 |
| WO | 9623010 A2 | 8/1996 |
| WO | 9827124 A1 | 6/1998 |
| WO | 9919280 A1 | 4/1999 |
| WO | 9962963 A1 | 12/1999 |
| WO | 9962967 A2 | 12/1999 |
| WO | 0020427 A1 | 4/2000 |
| WO | 0037175 A1 | 6/2000 |
| WO | 0068280 A1 | 11/2000 |
| WO | 0069923 A1 | 11/2000 |
| WO | 0110875 A1 | 2/2001 |
| WO | 0136379 A1 | 5/2001 |
| WO | 0136503 A1 | 5/2001 |
| WO | 0138270 A1 | 5/2001 |
| WO | 0147839 A1 | 7/2001 |
| WO | 0148028 A1 | 7/2001 |
| WO | 0158874 A1 | 8/2001 |
| WO | 0168572 A1 | 9/2001 |
| WO | 0168725 A2 | 9/2001 |
| WO | 0174830 A1 | 10/2001 |
| WO | 0183447 A2 | 11/2001 |
| WO | 0200339 A2 | 1/2002 |
| WO | 0204119 A1 | 1/2002 |
| WO | 200210133 A1 | 2/2002 |
| WO | 0228805 A2 | 4/2002 |
| WO | 0234701 A1 | 5/2002 |
| WO | 02066404 A1 | 8/2002 |
| WO | 02066405 A1 | 8/2002 |
| WO | 02079276 A2 | 10/2002 |
| WO | 02083306 A2 | 10/2002 |
| WO | 02083306 A3 | 10/2002 |
| WO | 0296919 A1 | 12/2002 |
| WO | 03004158 A2 | 1/2003 |
| WO | 03011876 A1 | 2/2003 |
| WO | 03024902 A1 | 3/2003 |
| WO | 0359511 A1 | 7/2003 |
| WO | 03053890 A1 | 7/2003 |
| WO | 03053891 A1 | 7/2003 |
| WO | 04043887 A2 | 5/2004 |
| WO | 2004056477 A1 | 7/2004 |
| WO | 2004056478 A1 | 7/2004 |
| WO | 2004056479 A1 | 7/2004 |
| WO | 2004056480 A1 | 7/2004 |
| WO | 2004078799 A1 | 9/2004 |
| WO | 2005082816 A1 | 9/2005 |
| WO | 2005092821 A1 | 10/2005 |
| WO | 2005111099 A1 | 11/2005 |
| WO | 2006008438 A1 | 1/2006 |
| WO | 2006016101 A1 | 2/2006 |
| WO | 07021955 A2 | 2/2007 |
| WO | 2007024504 A1 | 3/2007 |
| WO | 2007059015 A1 | 5/2007 |
| WO | 2007080081 A2 | 7/2007 |
| WO | 2008038173 A2 | 4/2008 |
| WO | 2009085411 A1 | 11/2009 |

OTHER PUBLICATIONS

Boor, Jr., John, "Ziegler-natta catalysts and polymerizations,"1979, 1 cover page and 1 publishing page, Academic Press, Inc., New York.

Brintzinger, Hans H., et al., "Stereospecific olefin polymerization with chiral metallocene catalysts," Angew. Chem. Int. Ed. Engl., 1995, pp. 1143-1170, VCH Verlagsgesellschaft mbH, Weinheim.

Britovsek, George J. P., et al., "Oligomerisation of ethylene by bis(imino)pyridyliron and -cobalt complexes," Chem. Eur. J., 2000, pp. 2221-2231, vol. 6, No. 12, Wiley-VCH Verlag GmbH, Weinheim.

Foreign communication from a related counterpart application—International Search Report, PCT/US2004/004472, Jul. 16, 2004, 3 pages.

Foreign communication from a related counterpart application—International Search Report and Written Opinion, PCT/US2005/005437, Jul. 4, 2005, 13 pages.

Foreign communication from a related counterpart application—International Search Report and Written Opinion, PCT/US2005/042175, Aug. 17, 2006, 9 pages.

Foreign communication from a counterpart application—Written Opinion, SG 200605612-1, Aug. 28, 2007, 5 pages.

Foreign communication from a counterpart application No. CA 2,556,879 filed Feb. 18, 2005—Filing of Prior Art under Section 34.1 of the Patent Act Protest under Section 10 of the Patent Rules, Jan. 11, 2008, 11 pages.

Kumar, R. N., et al., "Mononuclear and binuclear complexes of Fe(II) and Cu(II) with 2,6-diacetyl pyridine monoxime and phenylene diamine," Jul.-Sep. 1999, pp. 964-969 plus 1 cover page, vol. 11, No. 3, Asian Journal of Chemistry.

"Preparation of iron- or cobalt-based polynuclear pyridine-containing diimine catalysts for olefin polymerization," XP-002284349, Jun. 14, 2004, 1 page, CAPLUS.

Nelson, S. Martin, et al., "Metal-ion controlled reactions of 2,6-diacetylpyridine with 1,2-diaminoethane and 2,6-diformylpyridine with o-phenylenediamine and the crystal and molecular structure of a pentagonal pyramidal cadmium (II) complex containing unidentate o-phenylenediamine," 1982, pp. 407-415, J.C.S. Dalton.

Office Action dated Apr. 19, 2007 (8 pages), U.S. Appl. No. 10/783,429, filed Feb. 20, 2004.

Office Action dated Aug. 8, 2007 (13 pages), U.S. Appl. No. 10/782,554, filed Feb. 19, 2004.

Office Action dated Sep. 28, 2007 (8 pages), U.S. Appl. No. 10/783,429, filed Feb. 20, 2004.

Office Action dated Feb. 7, 2008 (6 pages), U.S. Appl. No. 10/782,554, filed Feb. 19, 2004.

Office Action dated Jun. 26, 2008 (16 pages), U.S. Appl. No. 11/207,232, filed Aug. 19, 2005.

Office Action dated Dec. 8, 2008 (41 pages), U.S. Appl. No. 10/782,554, filed Feb. 19, 2004.

Office Action (Final) dated Feb. 3, 2009 (15 pages), U.S. Appl. No. 11/207,232, filed Aug. 19, 2005.

Ranwell, A., et al., "Potential application of ionic liquids for olefin oligomerization," Sasol Technology R&D, Sasolburg, South Africa, 2002, pp. 147-160, American Chemical Society.

Rao, Guo-Ying, et al., "Coordination mode of the Cr(2-ethylhexanoate)3/triethylaluminum/dimethylpyrrole/tetrachloroethane," 2003, pp. 80-82, vol. 30, No. 1, Journal of Beijing University of Chemical Technology, Beijing, China.

Reagen, W. K., "Chromium(II) and (III) pyrrolyl ethylene oligomerization catalysts. Synthesis and crystal structure of square planar Cr(NC4H4)4-2, and pentanuclear (Cr5(NC4H4)10(OC4H8)4)," Symposium on Novel Preparation and Conversion of Light Olefins presented before the division of Petroleum Chemistry, Inc., Sep. 10-15, 1989, pp. 583-588, American Chemical Society.

Schofer, Susan J., et al., "Studies of a chromium-based ethylene oligomerization system," 1 page, INOR 817.

Small, Brooke L., et al., "Highly active iron and cobalt catalysts for the polymerization of ethylene," Journal of the American Chemical Society, 1998, pp. 4049-4050 plus 1 cover page, vol. 120, No. 16, American Chemical Society.

Small, Brooke L., et al., "Iron-based catalysts with exceptionally high activities and selectivities for oligomerization of ethylene to linear a-olefins," Journal of the American Chemical Society, 1998, pp. 7143-7144 plus 1 cover page, American Chemical Society.

Small, Brooke L., et al., "Polymerization of propylene by a new generation of iron catalysts: mechanisms of chain initiation, propagation, and termination," Macromolecules, 1999, pp. 2120-2130, vol. 32, No. 7, American Chemical Society.

Sui, Junlong, et al., "Synthesis of 1—hexene by trimerization of ethylene," 2001, pp. 23-26, 43, vol. 18, No. 2, China Synthetic Resin and Plastics.

Tamura, Takao, "Recent trends in a -olefin manufacturing technology," Idemitsu Giho, 1995, pp. 266-269, vol. 38, No. 3.

Tobisch, Sven, et al., "Catalytic linear oligomerization of ethylene to higher a-olefins: insight into the origin of the selective generation of 1-hexene promoted by a cationic cyclopentadienyl-arene titanium active catalyst," Organometallics, 2003, pp. 5392-5405, vol. 22, No. 26, American Chemical Society.

Tobisch, Sven, et al., "Catalytic oligomerization of ethylene to higher linear a-olefins promoted by cationic group 4 cyclopentadienyl-arene active catalysts: a DFT investigation exploring the influence of electronic factors on the catalytic properties by modification of the hemilabile arene functionality," Organometallics, 2004, pp. 4077-4088, vol. 23, No. 17, American Chemical Society.

Tobisch, Sven, et al., "Catalytic oligomerization of ethylene to higher linear a-olefins promoted by cationic group 4 [(n5-Cp-(CMe2-bridge)-Ph)M11(ethylene)2]+ (M = Ti, Zr, Hf) active catalysts: a density functional investigation of the influence of the metal on the catalytic activity and selectivity," J. Am. Chem. Soc., 2004, pp. 9059-9071, vol. 126, No. 29, American Chemical Society.

Tobisch, Sven, et al., "Catalytic oligomerization of ethylene to higher linear a-olefins promoted by cationic group 4 cyclopentadienyl-arene active catalysts: toward the computational design of zirconium- and hafnium-based ethylene trimerization catalysts," Organometallics, 2005, pp. 256-265, vol. 24 No. 2, American Chemical Society.

Van Rensburg, Werner Janse, et al., "A DFT study toward the mechanism of chromium-catalyzed ethylene trimerization," Organometallics, 2004, pp. 1207-1222, vol. 23, No. 6, American Chemical Society.

Wu, Tianzhi, et al., "Catalytic trimerization of ethylene by half-sandwich titanium complexes bearing a pendant ethereal group," Journal of Molecular Catalysis A: Chemical, 2004, pp. 227-229, vol. 214, Elsevier B.V.

Yang, Y., et al., "Roles of chloro compound in homogeneous [Cr(2-ethylhexanoate)3/2,5-dimethylpyrrole/triethylaluminum/chlorocompound] catalyst system for ethylene trimerization," Applied Catalysis A: General, 2000, pp. 29-38, vol. 193, Elsevier Science B.V.

Ye, Zhibin, et al., "A tandem catalytic system for the synthesis of ethylene—hex-1-ene copolymers from ethylene stock," Macromol. Rapid Commun., 2004, pp. 647-652, vol. 25, Wiley-VCH Verlag GmbH & Co. KGaA, Weinheim.

Yu, Zhi-Xiang, "Theoretical studies of the mechanisms of ethene trimerization by Ta- and Cr-based catalysts," 1 page, INOR 857.

Yu, Zhi-Xiang, et al., "Why trimerization? Computational elucidation of the origin of selective trimerization of ethene catalyzed by [TaCl3(CH3)2] and an agostic-assisted hydride transfer mechanism," Angew. Chem. Int. Ed., 2003, pp. 808-811, vol. 42, No. 7, Wiley-VCH Verlag GmbH & Co. KGaA, Weinheim.

Agapie, Theodor, et al., "Mechanistic studies of the ethylene trimerization reaction with chromium—diphosphine catalysts: experimental evidence for a mechanism involving metallacyclic intermediates," J. Am. Chem. Soc. 2004, pp. 1304-1305, vol. 126, No. 5, American Chemical Society.

Agapie, Theodor, et al., "Structural and mechanistic studies of a chromium—diphosphine system for catalytic trimerization of ethylene," INOR 494, Mar. 28-Apr. 1, 2004, 1 page, The 227th ACS National Meeting, Anaheim, California.

"Aldrich," Catalog Handbook of Fine Chemicals, Aldrich Chemical Company, 1990-1991, Cover page, Information Sheet, and pp. 1274-1275.

Alobaidi, Fahad, et al., "Direct synthesis of linear low-density polyethylene of ethylene/1-hexene from ethylene with a tandem catalytic system in a single reactor," Journal of Polymer Science: Part A: Polymer Chemistry, 2004, pp. 4327-4336, vol. 42, Wiley Periodicals, Inc.

Andes, Cecily, et al., "Formation of an ethene trimerization catalyst from (CH3)2TACL3," 1 page, INOR 261.

Andes, Cecily, et al., "New tantalum catalyst for the selective trimerization of ethene," 1 page, INOR 273.

Andes, Cecily, et al., "New tantalum-based catalyst system for the selective trimerization of ethene to 1-hexene," J. Am. Chem. Soc., 2001, pp. 7423-7424, vol. 123, No. 30, American Chemical Society.

Blok, Arno N. J., et al., "Mechanism of ethene trimerization at an ansa-(arene) (cyclopentadienyl) titanium fragment," Organometallics, 2003, pp. 2564-2570, vol. 22, No. 13, American Chemical Society.

Bollmann, Annette, et al., "Ethylene tetramerization: a new route to produce 1-octene in exceptionally high selectivities," J. Am. Chem. Soc., 2004, pp. 14712-14713, vol. 126, No. 45, American Chemical Society.

Briggs, John R., "The selective trimerization of ethylene to hex-1-ene," 1989, pp. 674-675, J. Chem. Soc., Chem. Commun.

Carter, Anthea, et al., "High activity ethylene trimerisation catalysts based on diphosphine ligands," Chem. Commun., 2002, pp. 858-859, The Royal Society of Chemistry.

Chen, Jwu-Ting, et al., "Dimerization and oligomerization of ethylene catalyzed by a palladium(II) complex with imine-phosphine ligand," 2000, pp. 279-281, vol. 47, No. 1, Journal of the Chinese Chemical Society.

Dai, Changhua, "Commercialization of 1-hexene by ethylene trimerization in China," Nov. 2002, pp. 25-29, vol. 10, No. 11, Petroleum & Petrochemical Today.

De Bruin, Theodorus J. M., et al., "Hemilabile ligand induced selectivity: a DFT study on ethylene trimerization catalyzed by titanium complexes," Organometallics, 2003, pp. 3404-3413, vol. 22, No. 17, American Chemical Society.

De Wet-Roos, Deon, et al., "Homogeneous tandem catalysis of bis(2-decylthioethyl)amine—chromium trimerization catalyst in combination with metallocene catalysts," Macromolecules, 2004, pp. 9314-9320, vol. 37, No. 25, American Chemical Society.

Deckers, Patrick J. W., et al., "Catalytic trimerization of ethene with highly active cyclopentadienyl—arene titanium catalysts," Organometallics, 2002, pp. 5122-5135, vol. 21, No. 23, American Chemical Society.

Deckers, Patrick J. W., et al., "Switching a catalyst system from ethene polymerization to ethene trimerization with a hemilabile ancillary ligand," Angew. Chem. Int. Ed., 2001, pp. 2516-2519, vol. 40, No. 13, Wiley-VCH Verlag GmbH, D-69451 Weinheim.

Dixon, John T., et al., "Advances in selective ethylene trimerisation—a critical overview," Journal of Organometallic Chemistry, 2004, pp. 3641-3668, vol. 689, Elsevier B.V.

Emrich, Rainer, "The role of metallacycles in the chromium-catalyzed trimerization of ethylene," Organometallics, Apr. 15, 1997, pp. 1511-1513, vol. 16, No. 8, American Chemical Society.

Fang, Yiqun, et al., "A new chromium-based catalyst coated with paraffin for ethylene oligomerization and the effect of chromium state on oligomerization selectivity," Applied Catalysis A: General, 2002, pp. 33-38, vol. 235, Elsevier Science B.V.

Foreign communication from a related counterpart application—International Search Report and Written Opinion, PCT/US2005/005416, Jun. 1, 2005, 10 pages.

Foreign communication from a related counterpart application—International Search Report and Written Opinion, PCT/US2006/031303, Dec. 19, 2006, 13 pages.

Foreign communication from a related counterpart application—EP Examination Report, 05723396.7-2109, Oct. 10, 2007, 4 pages.

Foreign communication from a counterpart application—International Search Report and Written Opinon, PCT/US2008/083026, Mar. 19, 2009, 9 pages.

Freemen, J. W., et al., "Selective production of 1-hexene from ethylene," Florida Catalysis Conference, Apr. 19-23, 1999, 30 pages.

Hessen, Bart, "Monocyclopentadienyl titanium catalysts: ethene polymerisation versus ethene trimerisation," Journal of Molecular Catalysis A: Chemical, 2004, pp. 129-135, vol. 213, Elsevier B.V.

Huang, Jiling, et al., "Ethylene trimerization with a half-sandwich titanium complex bearing a pendant thienyl group," Chem Commun, 2003, pp. 2816-2817, The Royal Society of Chemistry.

Jiang, Tao, et al., "Research advances of 1—hexene process by ethylene trimerization," Oct. 2000, pp. 284-287, vol. 18, No. 5, Petrochemical Technology & Application.

Köhn, R. D., et al., "Olefin trimerization with 1,3,5-triazacyclohexane complexes of chromium," INOR 278, 2 pages.

Köhn, Randolf D., et al., "1,3,5-Triazacyclohexane complexes of chromium as homogeneous model systems for the phillips catalyst," 2003, pp. 88-100, American Chemical Society.

Köhn, Randolf D., et al., "1,3,5-Triazacyclohexane complexes of chromium as homogeneous model systems for the phillips catalyst," pp. 147-155.

Köhn, Randolf D., et al., "Selective trimerization of a-olefins with triazacyclohexane complexes of chromium as catalysts," Angew. Chem. Int. Ed., 2000, pp. 4337-4339, vol. 39, No. 23, Wiley-VCH Verlag GmbH, D-69451 Weinheim.

Luo, He-Kuan, et al., "The effect of halide and the coordination geometry of chromium center in homogeneous catalyst system for ethylene trimerization," Journal of Molecular Catalysis A: Chemical, 2004, pp. 9-17, vol. 221, Elsevier B.V.

Mahomed, Hamdani, et al., "Ethylene trimerisation catalyst based on substituted cyclopentadienes," Applied Catalysis A: General, 2003, pp. 355-359, vol. 255, Elsevier B.V.

Manyik, R. M., et al., "A soluble chromium-based catalyst for ethylene trimerization and polymerization," Journal of Catalysis, 1977, pp. 197-209, vol. 47, Academic Press, Inc.

Mark, Herman, F., Editor, "Encyclopedia of polymer science and engineering," vol. 6, 1986, pp. 383-522 plus 1 cover page, 2 publishing pages, and 1 contents page, John Wiley & Sons, Inc., USA.

McGuinnes, David S., et al., "First Cr(III)—SNS complexes and their use as highly efficient catalysts for the trimerization of ethylene to 1-hexene," J. Am. Chem. Soc., 2003, pp. 5272-5273, vol. 125, No. 18, American Chemical Society.

McGuinnes, David S., et al., "Novel Cr-PNP complexes as catalysts for the trimerisation of ethylene," Chem. Commun., 2003, pp. 334-335, The Royal Society of Chemistry.

Meijboom, Nicolaas, et al., "Organometallic chemistry of chromium(VI): synthesis of chromium(VI) alkyls and their precursors. X-ray crystal structure of the metallacycle Cr(NtBu)2{o-(CHSiMe3)2C6H4}," Organometallics, 1990, pp. 774-782, vol. 9, No. 3, American Chemical Society.

Mihan, Shahram, et al., "Triazacyclohexane complexes of chromium for selective trimerization," 1 page, INOR 114.

Monoi, Takashi, et al., "Silica-supported Cr[N(SiMe3)2]3/isobutylalumoxane catalyst for selective ethylene trimerization," Journal of Molecular Catalysis A: Chemical, 2002, pp. 135-141, vol. 187, Elsevier Science B.V.

Morgan, David H., et al., "The effect of aromatic ethers on the trimerisation of ethylene using a chromium catalyst and aryloxy ligands," Adv. Synth. Catal., 2003, pp. 939-942, vol. 345, Wiley-VCH Verlag GmbH & Co. KGaA, Weinheim.

Ninanalov, I. I., et al., "Equilibrium of the trimerization of ethylene into hexenes," Ref. Zh., Khim, Abstract No. 24B897, 1983, 2 pages, Copyright 2003, ACS.

Office Action dated May 24, 2005 (6 pages), U.S. Appl. No. 10/783,429, filed Feb. 20, 2004.

Office Action dated Aug. 31, 2005 (13 pages), U.S. Appl. No. 10/783,429, filed Feb. 20, 2004.

Office Action dated Jan. 18, 2006 (15 pages), U.S. Appl. No. 10/783,429, filed Feb. 20, 2004.

Office Action dated May 24, 2006 (8 pages), U.S. Appl. No. 10/783,429, filed Feb. 20, 2004.

Office Action dated Sep. 7, 2006 (4 pages), U.S. Appl. No. 10/783,429, filed Feb. 20, 2004.

Office Action dated Jan. 9, 2007 (13 pages), U.S. Appl. No. 10/783,429, filed Feb. 20, 2004.

Office Action dated Nov. 28, 2008 (43 pages), U.S. Appl. No. 12/057,853, filed Mar. 28, 2008.

Esteruelas, Miguel A., et al., "Preparation, Strucutre and Ethylene Polymerization Behavior of Bis (imino) pyridyl Chromium(III) Complexes," Organometallics—American Chemical Society, Jan. 1, 2003, pp. 395-406, vol. 22.

Small, Brooke L, et al., "Iron Catalysts for the Head-to-Head Dimerization of a-Olefins and Mechanistic Implications for the Production of Linear a-Olefins," Organometallics—American Chemical Society, Nov. 22, 2001, pp. 5738-5744, vol. 20.

Foreign communication from a related counterpart application—International Preliminary Report on Patentability, PCT/US2005/005416, Aug. 22, 2006, 6 pages.

Foreign communication from a related counterpart application—International Preliminary Report on Patentability, PCT/US2006/031303, Feb. 20, 2008, 7 pages.

Office Action dated Jun. 12, 2009, (53 pages) U.S. Appl. No. 11/928,756, filed Oct. 30, 2007.

Office Action (Final) dated Aug. 3, 2009 (20 pages), U.S. Appl. No. 12/057,853, filed Mar. 28, 2008.

Patent application entitled "Methods of Preparation of an Olefin Oligomerization Catalyst," by Ronald Knudsen, filed on Aug. 17, 2009 as U.S. Appl. No. 12/534,536.

Foreign communication from a counterpart application, EP 05723396.7, Examination Report, Mar. 8, 2010, 3 pages.

Foreign communication from a counterpart application, EP05723401.5, Examination Report, May 4, 2010, 7 pages.

Foreign communication from a counterpart application, AU 2006283779—Examination Report, Jun. 11, 2010, 2 pages.

Foreign communication from a counterpart application, PCT/US2008/087310, International Preliminary Report on Patentability, Jun. 22, 2010, 7 pages.

Office Action (Final) dated Feb. 4, 2010, (23 pages), U.S. Appl. No. 11/928,756, filed Oct. 30, 2007.

Office Action (Final) dated Apr. 28, 2010, (11 pages), U.S. Appl. No. 11/928,756, filed Oct. 30, 2007.

Office Action dated Jun. 21, 2010 (15 pages), U.S. Appl. No. 12/534,536, filed Aug. 3, 2009.

Foreign communication from a counterpart application CA2664894, Examination Report, Apr. 30, 2010, 4 pages.

Notice of Allowance dated Jun. 15, 2010 (11 pages), U.S. Appl. No. 11/928,756 filed Oct. 30, 2007.

Advisory Action dated May 21, 2009 (3 pages), U.S. Appl. No. 11/207,232, filed Aug. 19, 2005.

* cited by examiner

PROCESSES FOR DIMERIZING OR ISOMERIZING OLEFINS

CROSS-REFERENCE TO RELATED APPLICATIONS

The subject matter of the present application is related to U.S. Pat. No. 7,045,632; U.S. Patent Publication Nos. 2006/0128958 and 2005/0187418 and U.S. patent application Ser. No. 11/207,232 filed Aug. 19, 2005 and entitled "Methods of Preparation of an Olefin Oligimerization Catalyst" and Ser. No. 11/009,916 filed Dec. 10, 2004 and entitled "Methods for Producing a Hexadentate Bimetallic Complex," each of which is hereby incorporated herein by reference in its entirety for all purposes.

TECHNICAL FIELD

The present disclosure relates to catalysts and catalyst systems for producing olefin dimers or for isomerizing olefins.

BACKGROUND

Olefins are important items of commerce. Their many applications include employment as intermediates in the manufacture of detergents, as more environmentally friendly replacements where refined oils might otherwise be used, as monomers, and as intermediates for many other types of products.

The dimerization and/or the isomerization of olefins by transition metal complexes represents an important class of industrially relevant chemistry. The major types of commercially used catalysts for these reactions are alkylaluminum compounds, certain nickel-phosphine complexes, and a titanium halide with a Lewis acid such as diethylaluminum chloride (DEAC). Thus, it would be desirable to develop other catalyst systems and methods of using same for the production of linear dimers and/or the isomers of olefins.

SUMMARY OF THE INVENTION

Disclosed herein is a process for dimerizing alpha olefins comprising contacting (i) an alpha olefin having at least 3 carbon atoms, (ii) a hexadentate bimetallic catalyst, and (iii) a cocatalyst, and dimerizing the alpha olefin in a reaction zone at conditions effective to dimerize an alpha olefin to form a reaction zone effluent comprising alpha olefin oligomers including alpha olefin dimers.

Also disclosed herein is a process for dimerizing olefins comprising contacting (i) an alpha olefin having at least 3 carbon atoms, (ii) a hexadentate bimetallic complex comprising a cobalt compound, and (iii) a cocatalyst, and dimerizing the alpha olefin in a reaction zone at conditions effective to dimerize an alpha olefin to form a reaction zone effluent comprising oligomers including dimmers, wherein greater than 20 weight percent of the alpha olefin has been converted to oligomers, greater than 30 weight percent of the oligomers are dimers, and greater than 85 mole percent of the dimers are linear.

Further disclosed herein is a process to isomerize alpha olefins comprising contacting (i) an alpha olefin having at least 6 carbon atoms, (ii) a hexadentate bimetallic complex comprising two cobalt compounds complexed to a hexadentate ligand, and (iii) a cocatalyst, and isomerizing the alpha olefin in a reaction zone at conditions effective to isomerize the alpha olefin to form a reaction zone effluent comprising isomerized alpha olefins.

DETAILED DESCRIPTION OF THE INVENTION

Disclosed herein are processes for dimerizing olefins utilizing a catalyst system comprising a catalyst component. Also disclosed herein are processes for isomerizing an olefin utilizing a catalyst system comprising a catalyst component. The catalyst system for the olefin dimerization process or the olefin isomerization process may further comprise a cocatalyst component. The catalyst component may be a metal complex comprising a metal compound complexed to a heteroatomic ligand. Additional details of the catalyst component (e.g., heteroatomic ligand, metal compound, etc . . . ) and cocatalyst component are disclosed herein.

For purposes of this application, an acyl group is represented by the structure $RC(\!\!=\!\!O)\!\!-\!\!$, wherein R may be hydrogen, a hydrocarbyl group, a substituted hydrocarbyl group, an alkyl group, or a substituted alkyl group.

For purposes of this application, the term "hydrocarbon(s)" refers to compounds or groups containing only carbon and hydrogen. For purposes of this application, the term "hydrocarbyl(s)" or "hydrocarbyl group(s)" refers to a univalent group(s) derived by removal of one hydrogen atom from a carbon atom of a "hydrocarbon." For purposes of this application, the term "hydrocarbylene(s)" or "hydrocarbylene group(s)" refers to a divalent group(s) derived by removal of two hydrogen atoms from one carbon atom or one hydrogen from two different carbon atoms of a "hydrocarbon." If not otherwise stated, the "hydrocarbon(s)", "hydrocarbyl groups," or "hydrocarbylene groups" herein may contain from 1 to 30 carbon atoms. For the purposes of this application, the term "alkyl(s)" or "alkyl group(s)" refers to a univalent group derived by removal of a hydrogen atom from any carbon atom of an alkane. For the purposes of this application, the term "alkylene(s)" or "alkylene group(s)" refers to a divalent group derived by removal of two hydrogen atoms from one carbon atom or one hydrogen atom from two different carbon atoms of an alkane. If not otherwise stated, the "alkyl group(s)" and "alkylene group(s)" herein may contain from 1 to 30 carbon atoms.

For purposes of this application, the term "substituted hydrocarbon(s)" and its derivatives (e.g. "substituted hydrocarbyl" and "substituted hydrocarbylene") refer to hydrocarbon compounds or groups which contains one or more substituent groups which are inert under the process conditions to which the compound containing these groups is subjected. Similarly, the term "substituted alkyl" and "substituted alkylene" refers to an "alkyl group" or "alkylene group," respectively, which contains one or more substituent groups which are inert under the process conditions to which the compound containing these groups is subjected. The substituent groups also do not substantially interfere with the process for preparation of the catalysts disclosed herein. If not otherwise stated, the "substituted hydrocarbyl," "substituted hydrocarbyl," "substituted hydrocarbylene," "substituted alkyl," and "substituted alkylene" groups herein may contain from 1 to 30 carbon atoms. Included in the meaning of "substituted" are aromatic and/or heteroaromatic rings.

For purposes of this application, the term "inert functional group(s)" refers to a group(s), other than hydrocarbyl, substituted hydrocarbyl, alkyl, or substituted alkyl, which does not substantially interfere with any process described herein where the compound in which it is present takes part. Examples of inert functional groups include halo (fluoro, chloro, bromo and iodo), or ethers such as —OR$_{18}$ wherein R$_{18}$ is hydrocarbyl, substituted hydrocarbyl, alkyl, or substituted alkyl. In cases in which the functional group may be near a metal atom, the functional group should not coordinate to the metal atom more strongly than the groups in compounds which are shown as coordinating to the metal atom that is they should not displace the desired coordinating group.

For purposes of this application, a primary carbon group includes a group of the formula —CH$_2$—, wherein the free valence is to any other atom. Thus, the free valence may be bonded to a hydrogen atom, halogen atom, carbon atom, oxygen atom, sulfur atom, etc. In other words, the free valence may be to hydrogen, hydrocarbyl, substituted hydrocarbyl, alkyl, substituted alkyl, or a functional group (e.g. an inert functional group). Examples of primary carbon groups include —CH$_3$, —CH$_2$CH(CH$_3$)$_2$, —CH$_2$Cl, —CH$_2$C$_6$H$_5$, and —CH$_2$OCH$_3$.

For purposes of this application, a secondary carbon group includes a group of the formula —CH=, wherein the free valences are to any other atoms. Thus, the free valences may be bonded to a halogen atom, carbon atom, oxygen atom, sulfur atom, etc. In other words, the free valences may be to a hydrocarbyl, a substituted hydrocarbyl, alkyl, substituted alkyl, or a functional group (e.g. an inert functional group). Specific examples of secondary carbon groups include —CH(CH$_3$)$_2$, —CHCl$_2$, —CH(C$_6$H$_5$)$_2$, cyclohexyl, —CH(CH$_3$)OCH$_3$, and —CH=CHCH$_3$.

For purposes of this application, a tertiary carbon group includes a group of the formula —C≡, wherein the free valences are to any other atoms. Thus, the free valences may be bonded to a halogen atom, carbon atom, oxygen atom, sulfur atom, etc. In other words, the free valences may be to a hydrocarbyl, a substituted hydrocarbyl, alkyl, substituted alkyl, or a functional group (e.g. an inert functional group). Examples of tertiary carbon groups include: —C(CH$_3$)$_3$, —C(C$_6$H$_5$)$_3$, —CCl$_3$, —C(CH$_3$)$_2$OCH$_3$, —C≡CH, —C(CH$_3$)CH=CH$_2$, C$_6$H$_5$, CF$_3$, 1-adamantyl.

The term "alpha olefin" whenever used in this specification and claims refers to an olefin that has a double bond between the first and second carbon atom of the longest contiguous chain of carbon atoms. The term "alpha olefin" includes linear and branched alpha olefins unless expressly stated otherwise. In the case of branched alpha olefins, a branch may be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. The term "alpha olefin," by itself, does not indicate the presence or absence of heteroatoms and/or the presence or absence of other carbon-carbon double bonds unless explicitly indicated. The terms "hydrocarbon alpha olefin" or "alpha olefin hydrocarbon" refer to alpha olefin compounds containing only hydrogen and carbon.

The term "linear alpha olefin" whenever used in this specification and claims refers to a linear olefin having a double bond between the first and second carbon atom. The term "linear alpha olefin" does not indicate the presence or absence of heteroatoms and/or the presence or absence of other carbon-carbon double bonds unless explicitly indicated. The terms "linear hydrocarbon alpha olefin" or "linear alpha olefin hydrocarbon" refers to linear alpha olefin compounds containing only hydrogen and carbon.

The term "normal alpha olefin" whenever used in this specification and claims refers to a linear hydrocarbon mono-olefin having a double bond between the first and second carbon atom. It should be noted that "normal alpha olefin" is not synonymous with "linear alpha olefin" as the term "linear alpha olefin" can include linear olefinic compounds having a double bond between the first and second carbon atoms and having heteroatoms and/or additional double bonds.

The term "consists essentially of normal alpha olefin(s)," or variations thereof, whenever used in this specification and claims refers to commercially available normal alpha olefin product(s). The commercially available normal alpha olefin product can contain non-normal alpha olefin impurities such as vinylidenes, internal olefins, branched alpha olefins, paraffins, and diolefins, among other impurities, which are not removed during the normal alpha olefin production process. One of ordinary skill in the art will recognize that the identity and quantity of the specific impurities present in the commercial normal alpha olefin product will depend upon the source of commercial normal alpha olefin product. Consequently, the term "consists essentially of normal alpha olefins" and its variants is not intended to limit the amount/quantity of the non-linear alpha olefin components any more stringently than the amounts/quantities present in a particular commercial normal alpha olefin product unless explicitly stated. One source of commercially available alpha olefins products are those produced by the oligomerization of ethylene. A second source of commercially available alpha olefin products are those which are produced, and optionally isolated from, Fischer-Tropsch synthesis streams One source of commercially available normal alpha olefin products produced by ethylene oligomerization which may be utilized as an olefin feedstock is Chevron Phillips Chemical Company LP, The Woodlands, Tex. Other sources of commercially available normal alpha olefin products produced by ethylene oligomerization which may be utilized as an olefin feedstock include Inneos Oligomers (Feluy, Belgium), Shell Chemicals Corporation (Houston, Tex. or London, United Kingdom), Idemitsu Kosan (Tokyo, Japan), and Mitsubishi Chemical Corporation (Tokyo, Japan) among others. One source of commercially available normal alpha olefin products produced, and optionally isolated from Fisher-Tropsch synthesis streams includes Sasol (Johannesburg, South Africa) among others.

Generally, a catalyst suitable for use in the dimerization or isomerization of olefins comprises a metal compound complexed to a heteroatomic ligand. The heteroatomic ligand may be a multidentate ligand (i.e., having the ability to form more than one complexing bond to metal compound). In an embodiment, the heteroatomic ligand is a multidentate ligand having a denticity of six and is termed a hexadentate ligand. In some embodiments, the hexadentate ligand comprises, or consists essentially of, two bisimine pyridine ligands. Examples of such hexadentate ligands include without limitation compounds having the structures of Ligands 1-10 shown in Table 1.

TABLE 1
Hexadentate Ligands
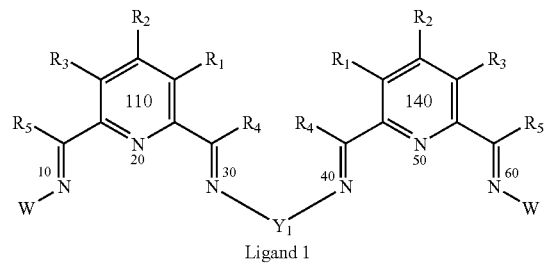
Ligand 1
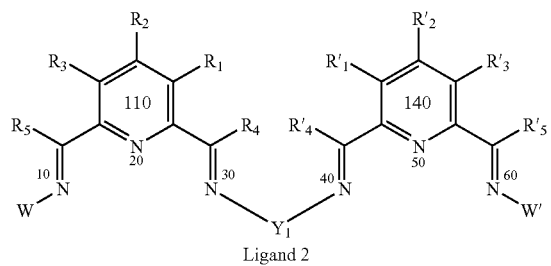
Ligand 2
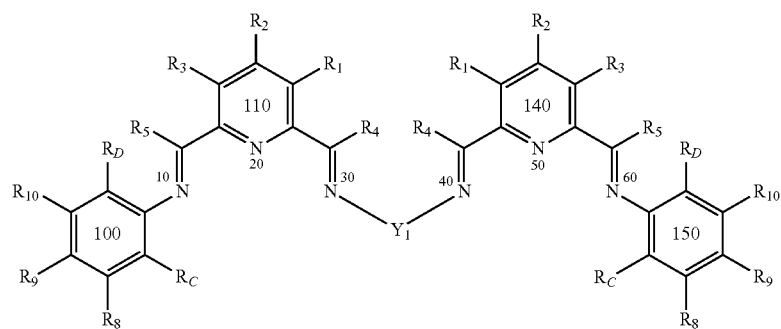
Ligand 3
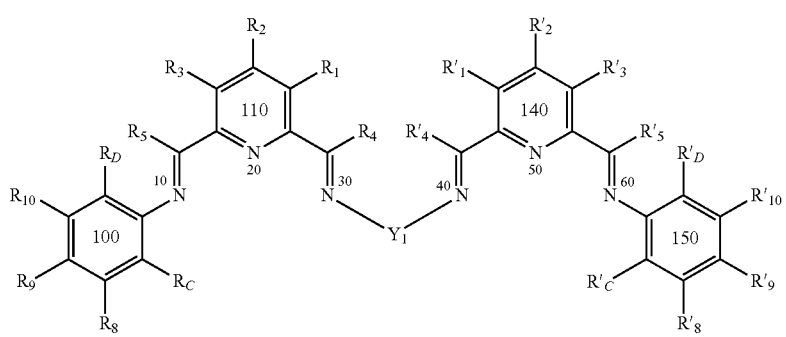
Ligand 4

TABLE 1-continued
Hexadentate Ligands
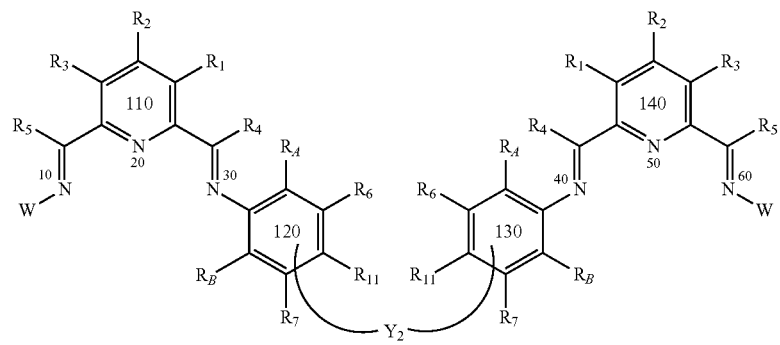
Ligand 5
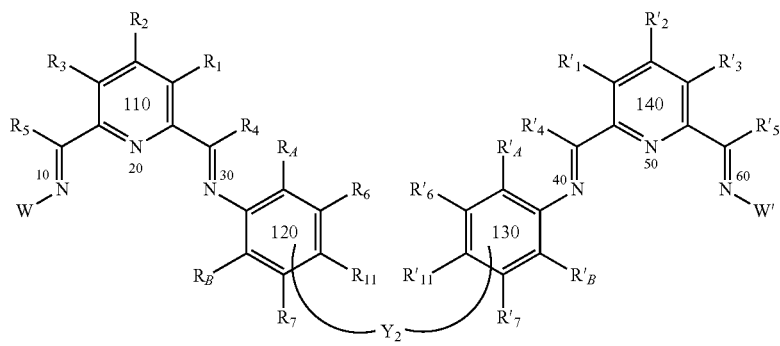
Ligand 6
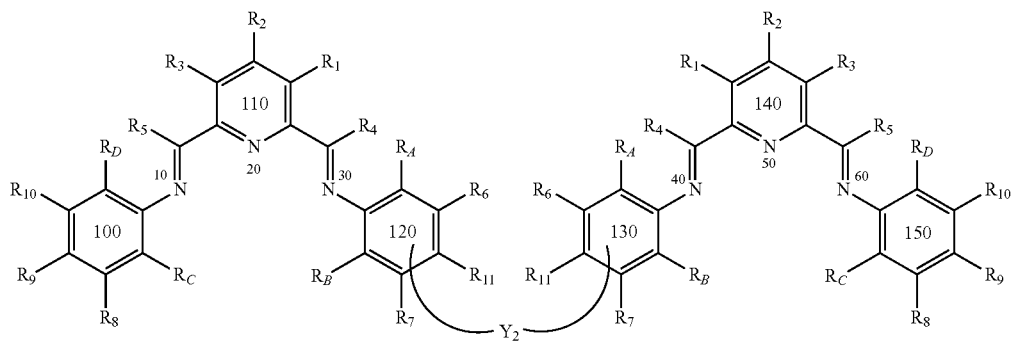
Ligand 7
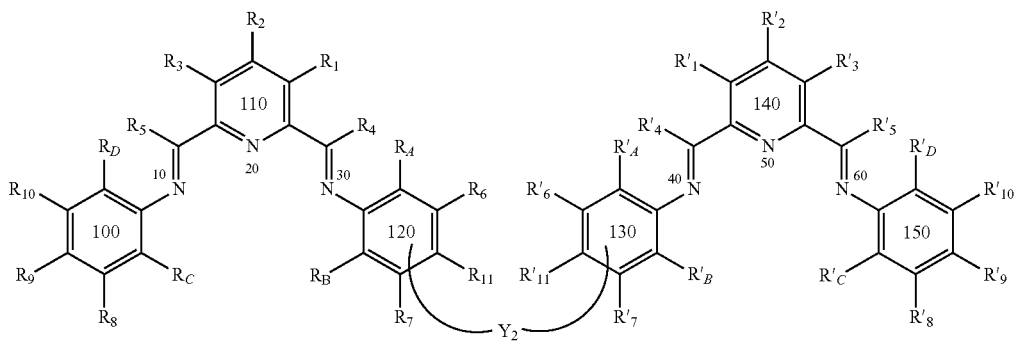
Ligand 8

TABLE 1-continued

Hexadentate Ligands

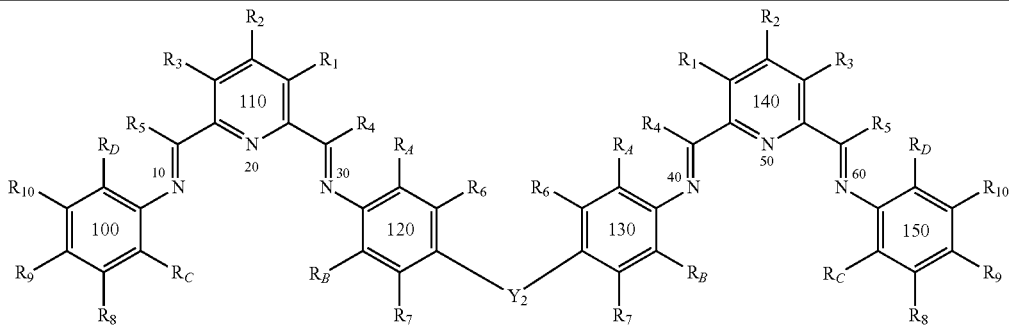

Ligand 9

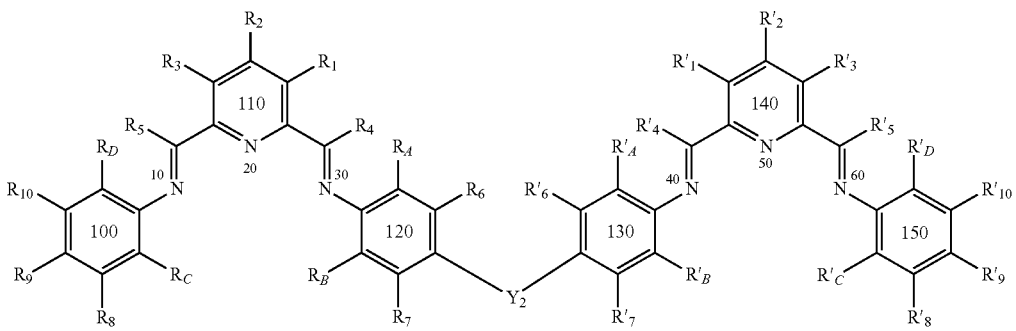

Ligand 10

Generally, the catalyst comprises a complex wherein at least two metal compounds are coordinated to a multidentate ligand. In an embodiment, the catalyst for the olefin dimerization or olefin isomerization processes comprises two metal compounds complexed to a hexadentate ligand. Suitable metal compounds will be described in more detail later herein. A catalyst complex comprising two metal compounds and a hexadentate ligand is hereafter referred to as a hexadentate bimetallic complex (HBC). In some embodiment, the hexadentate bimetallic complex comprises, or consists essentially of, two metal compounds complexed to a hexadentate ligand comprising two bisimine pyridine moieties. Examples of HBCs suitable for use in this disclosure include without limitation compounds having the structures of HBCs 1-10 shown in Table 2.

TABLE 2

Hexadentate Bimetallic Complexes

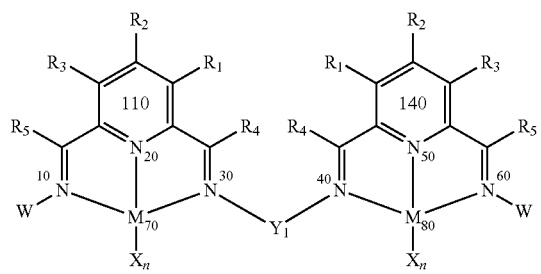

HBC 1

TABLE 2-continued
Hexadentate Bimetallic Complexes
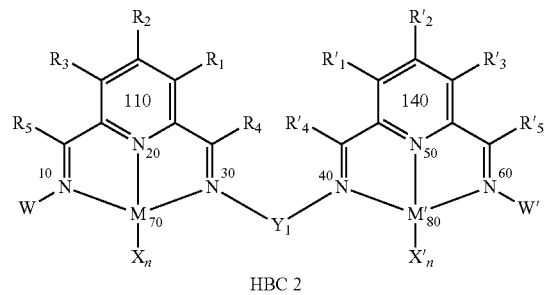
HBC 2
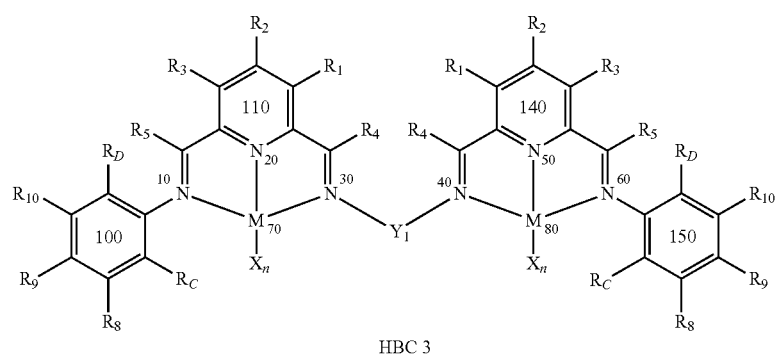
HBC 3
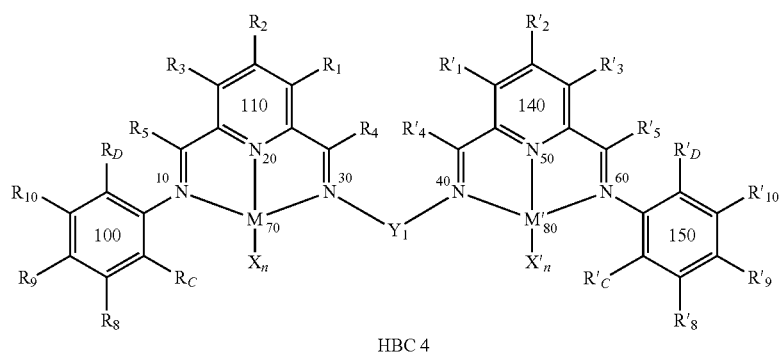
HBC 4
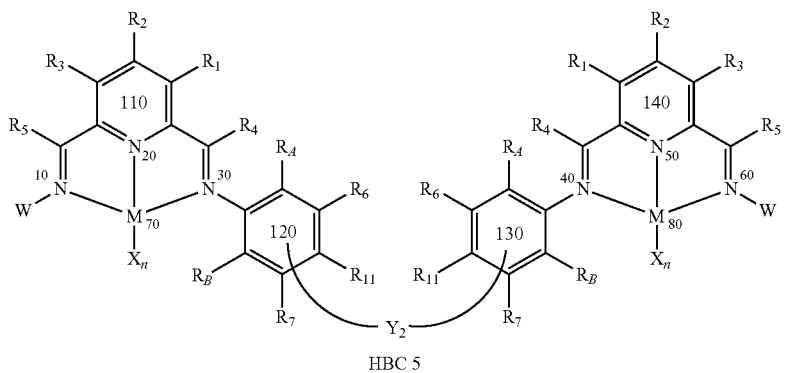
HBC 5

TABLE 2-continued
Hexadentate Bimetallic Complexes
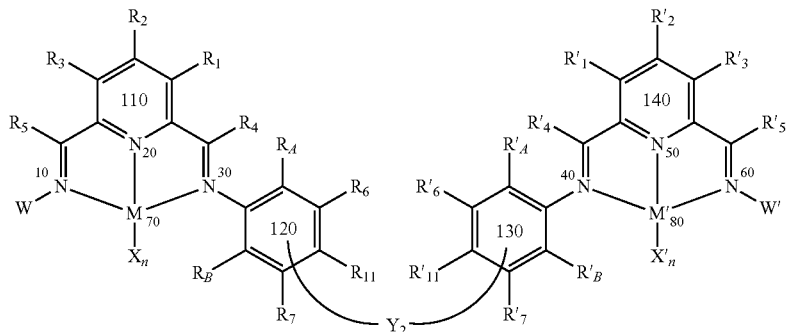
HBC 6
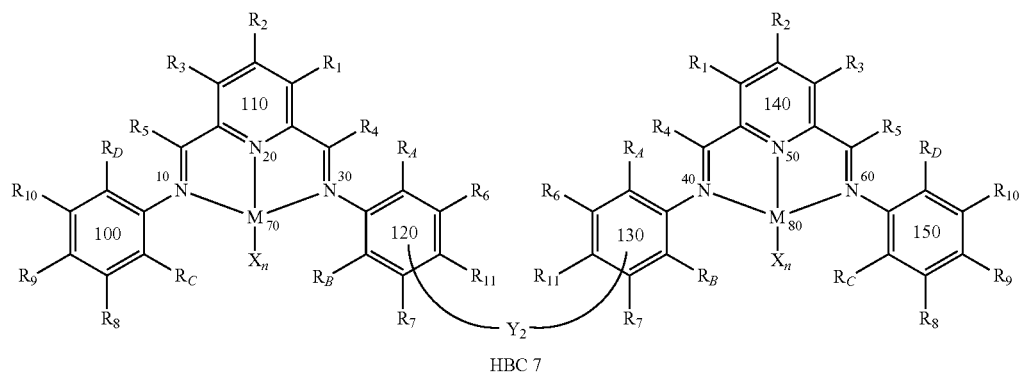
HBC 7
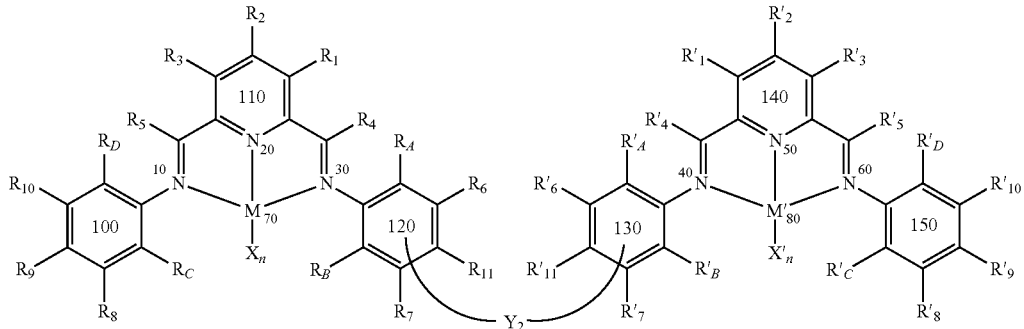
HBC 8
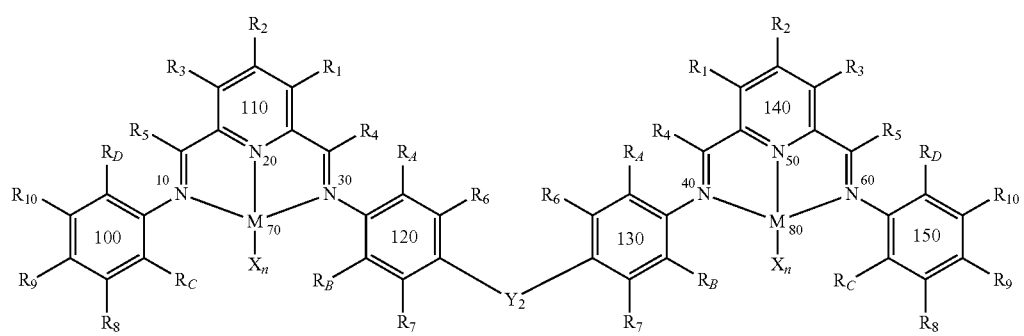
HBC 9

TABLE 2-continued

Hexadentate Bimetallic Complexes

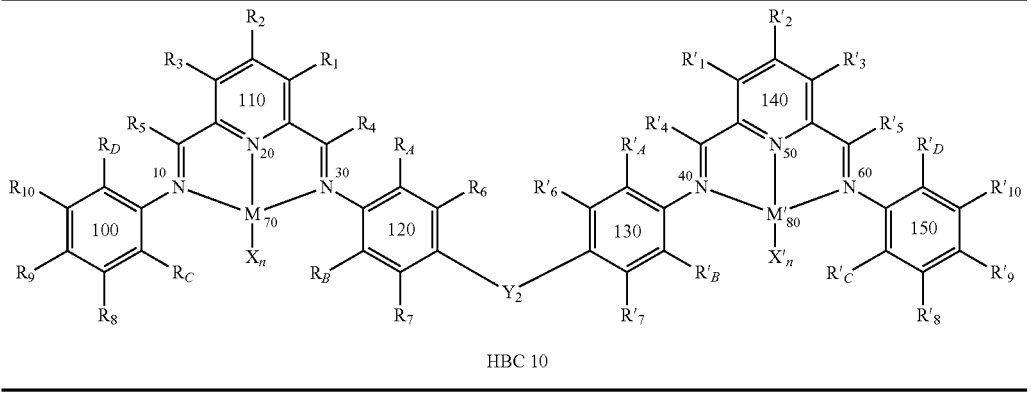

HBC 10

In some embodiments, the hexadentate ligand or HBC may be identified by six nitrogen atoms denoted by reference numerals 10, 20, 30, 40, 50, and 60 in Ligands 1-10 and HBCs 1-10. Using HBC 1 as an example, such hexadentate structures may be viewed as consisting of two halves or sides; one side including nitrogen atoms 10, 20, and 30, and the other side including nitrogen atoms 40, 50, and 60. The two halves may be connected by a structural bridge, such as $Y_1$. Alternatively, the two halves may be connected by two aromatic rings linked by structural bridge, $Y_2$ (see for example HBC 5). Additionally, the similarities between the two halves of the ligand or complex may vary. In various instances, the two halves may be mirror images of each other, identical or different, symmetrical or asymmetrical, planar or non-planar. The pendant groups, W, W', $R_n$, and $R'_n$, and linking groups, $Y_1$ and $Y_2$, are further defined below. The hexadentate metal complexes shown in Table 2 may be identified by the presence of two metal compounds (M-$X_n$ and M'-$X'_n$), which are complexed to a hexadentate ligand. The metal compounds are designated by reference numerals 70 and 80 in the structures of Table 2. The metal compound at site 70 (M-$X_n$) may be the same as or different than the metal compound at site 80 (M'-$X'_n$).

The metal complexes may be symmetrical or asymmetrical. The asymmetry may be a result of a difference between the terminal W and W' imine groups, differences among one or more of the substituents or the substituent pattern of the terminal imine aromatic rings 100 and 150, differences between the $R_4$ and $R'_4$ groups, differences between the $R_5$ and $R'_5$ groups, differences among one or more of the substituents or the substituent pattern of the pyridine rings 110 and 140, asymmetry in the linking group, $Y_1$, differences among one or more of the substituents or the substituent pattern of the linking aromatic rings 120 and 130, asymmetry in the linking group, $Y_2$, or any combination of differences in these elements. Variations in chemical structure orientation and planarity, such as may occur by rotation of a portion of a structure at a chemical bond, may also affect symmetry. Though technically a point of asymmetry, for the purpose of this discussion, a difference in the metal compound at sites 70 and 80 (either at the metal atom or the X groups) will not be considered a difference that affects the symmetry of the HBC. As an example, the link between symmetrical and asymmetrical embodiments may be illustrated where HBC 1 represents a symmetrical embodiment of HBC 2, if $Y_1$ is symmetrical, the terminal imine groups are identical, W and W' are identical, $R_4$ and $R'_4$ groups are identical, $R_5$ and $R'_5$ groups are identical, and the substituents and substituent pattern of the pyridine rings 110 and 140 are identical. Any difference in any one or more of these elements would make HBC 2 asymmetric. As a further example, HBC 7 would represent a symmetrical embodiment of HBC 8 where the R' groups of HBC 8 are selected to be identical to the R groups, and $Y_2$ is selected to be symmetrical. HBC 3 represents a specific symmetrical embodiment of HBC 1 wherein the aromatic rings 100 and 150 are substituted for the W and W' of HBC 2. HBC 7 represents a specific symmetrical embodiment of HBC 3 wherein the aromatic rings, 120 and 130, and structural bridge, $Y_2$, of HBC 8 are substituted for the structural bridge, $Y_1$, of HBC 3. Other symmetrical versus asymmetrical relationships among the structures in Table 1 and Table 2 will be apparent to one skilled in the art.

Components of the chemical structures illustrated in Table 1 and Table 2 may be subdivided into the following groups: Group 1—W and W'; Group 2—$R_1$, $R'_1$; $R_2$, $R'_2$, $R_3$, and $R'_3$; Group 3—$R'_4$, $R_5$, and $R'_5$; Group 4—$R_6$, $R'_6$, $R_7$, $R'_7$, $R_8$, $R'_8$, $R_9$, $R'_9$, $R_{10}$, $R'_{10}$, $R_{11}$ and $R'_{11}$; Group 5—$R_A$, $R'_A$, $R_B$, $R'_B$, $R_C$, $R'_C$, $R_D$, and $R'_D$; Group 6—$Y_1$ and $Y_2$; Group 7-M and M'; and Group 8—$X_n$, and $X'_n$. These groups are independent elements and thus the structures in Tables 1-2 may be defined using any combination of embodiments within each respective group.

In some embodiments, W and W' are each independently hydrogen, hydrocarbyl, substituted hydrocarbyl, alkyl, substituted alkyl, or an inert functional group. In an embodiment, W and/or W' are each independently an aromatic group, or a substituted aromatic group; alternatively, a phenyl group or a substituted phenyl group. The applicable inert functional groups are further described herein. In an embodiment, W and W' may be the same; or alternatively, W and W' may be different. Applicable hydrocarbyl group, substituted hydrocarbyl, alkyl, substituted alkyl, and inert functional groups are generally described herein and may be utilized to further identify W and W' of the ligand and catalyst.

In some embodiments, $R_1$, $R'_1$, $R_2$, $R'_2$, $R_3$, and $R'_3$ are each independently hydrogen, hydrocarbyl, substituted hydrocarbyl, alkyl, substituted alkyl, or an inert functional group. In other embodiments, any two of $R_1$, $R'_1$, $R_2$, $R'_2$, $R_3$, and $R'_3$, vicinal to one another, taken together may form a ring. In an embodiment and dependent upon the specific structure, $R_1$, $R_2$, and $R_3$, or $R_1$, $R'_1$, $R_2$, $R'_2$, $R_3$, and $R'_3$ may each be hydrogen. Applicable hydrocarbyl, substituted hydrocarbyl, alkyl, substituted alkyl, and inert functional groups are generally described herein and may be utilized to further identify $R_1$, $R_2$, and $R_3$, or $R_1$, $R'_1$, $R_2$, $R'_2$, $R_3$, and $R'_3$ of the ligand and catalyst.

In some embodiments, $R_4$, $R'_4$, $R_5$, and $R'_5$ are each independently hydrogen, hydrocarbyl, substituted hydrocarbyl, alkyl, substituted alkyl, or an inert functional group. Applicable hydrocarbyl group, substituted hydrocarbyl, alkyl, substituted alkyl, and inert functional groups are generally described herein and may be utilized to further identify $R_4$, and $R_5$, or $R_4$, $R'_4$, $R_5$, and $R'_5$ of the ligand and catalyst. In some embodiments $R_4$, and $R_1$, and/or $R'_4$, and $R'_1$, taken together may form a ring. In other embodiments $R_5$ and $R_3$, and/or $R'_5$ and $R'_3$, taken together may form a ring. In yet other embodiments, $R_4$ and $R_A$ or $R_B$, and/or $R'_4$ and $R'_A$ or $R'_B$, taken together may form a ring. In yet other embodiments, $R_5$ and $R_C$ or $R_D$, and/or $R'_5$ and $R'_C$ or $R'_D$, taken together may form a ring. In an embodiment and dependent upon the specific structure, $R_4$ and $R_5$, or $R_4$, $R'_4$, $R_5$, and $R'_5$ may each be a methyl group.

In some embodiments, $R_6$, $R'_6$, $R_7$, $R'_7$, $R_8$, $R'_8$, $R_9$, $R'_9$, $R_{10}$, $R'_{10}$, $R_{11}$ and $R'_{11}$ are each independently hydrogen, hydrocarbyl, substituted hydrocarbyl, or an inert functional group. Applicable hydrocarbyl group, substituted hydrocarbyl, alkyl, substituted alkyl, and inert functional groups are generally described herein and may be utilized to further identify $R_6$, $R_7$, $R_8$, $R_9$, $R_{10}$, and $R_{11}$, or $R_6$, $R'_6$, $R_7$, $R'_7$, $R_8$, $R'_8$, $R_9$, $R'_9$, $R_{10}$, $R'_{10}$, $R_{11}$ and $R'_{11}$ of the ligand and catalyst. In an embodiment and dependent upon the specific structure, $R_6$, $R_7$, $R_8$, $R_9$, $R_{10}$, and $R_{11}$, or $R_6$, $R'_6$, $R_7$, $R'_7$, $R_8$, $R'_8$, $R_9$, $R'_9$, $R_{10}$, $R'_{10}$, $R_{11}$ and $R'_{11}$ may each be hydrogen.

In some embodiments, $R_A$, $R'_A$, $R_B$, $R'_B$, $R_C$, $R'_C$, $R_D$, and $R'_D$, generally ortho to the nitrogen atom group, are each independently hydrogen, hydrocarbyl, substituted hydrocarbyl, alkyl, substituted alkyl, or an inert functional group. Applicable hydrocarbyl group, substituted hydrocarbyl, alkyl, substituted alkyl, and inert functional groups are further described herein and may be utilized to further identify $R_A$, $R_B$, $R_C$, and $R_D$, or $R_A$, $R'_A$, $R_B$, $R'_B$, $R_C$, $R'_C$, $R_D$, and $R'_D$ of the ligand and catalyst. In other embodiments, $R_A$, $R_B$, $R_C$, and $R_D$, or $R_A$, $R'_A$, $R_B$, $R'_B$, $R_C$, $R'_C$, $R_D$, and $R'_D$, are independently selected from hydrogen, fluorine, an inert functional group, a primary carbon group, a secondary carbon group, or a tertiary carbon group.

In an embodiment, the hydrocarbyl group, substituted hydrocarbyl group, alkyl group, or substituted alkyl group can be have from 1 to 30 carbon atoms; alternatively, from 2 to 20 carbon atoms; or alternatively, from 3 to 15 carbon atoms. In some embodiments, the substituents of the substituted hydrocarbyl group and the substituted alkyl group may be an inert functional group. In some embodiments, the hydrocarbyl group can be an aromatic group or substituted aromatic group; or alternatively, a phenyl group or a substituted phenyl group. In an embodiment, the aromatic group, substituted aromatic group, phenyl group, a substituted phenyl group can be have from 6 to 30 carbon atoms; alternatively, from 6 to 20 carbon atoms; or alternatively from 6 to 15 carbon atoms. In some embodiments, the substituents of any aromatic or phenyl group described herein may be an alkyl group, a substituted alkyl group, or an inert functional group. Applicable alkyl groups, a substituted alkyl groups, or an inert functional groups are generally described herein.

Generally, the alkyl group for any feature which calls for an alkyl group described herein can be can be a methyl, ethyl, n-propyl (1-propyl), isopropyl (2-propyl), n-butyl (1-butyl), sec-butyl (2-butyl), isobutyl (2-methyl-1-propyl), tert-butyl (2-methyl-2-propyl), n-pentyl (1-pentyl), 2-pentyl, 3-pentyl, 2-methyl-1-butyl, tert-pentyl (2-methyl-2-butyl), 3-methyl-1-butyl, 3-methyl-2-butyl, neo-pentyl (2,2-dimethyl-1-propyl), or n-hexyl (1-hexyl) group. Persons having ordinary skill in the art will readily recognize which alkyl group represents primary, secondary, or tertiary alkyl groups.

Generally, the inert functional group can be any functional group other than hydrocarbyl, substituted hydrocarbyl, alkyl, or substituted alkyl, which does not substantially interfer with the process(es) described herein in which the compound takes part. Examples of inert functional groups include halides and etheryl groups. In some embodiments, the halide inert functional group can be a fluoride, chloride, bromide, or iodide; alternatively, a fluoride. In an embodiment, the inert functional group can be an etheryl groups, (e.g. —$OR_{18}$). In some embodiments, the etheryl group can comprise from 1 to 20 carbon atoms; alternatively, from 1 to 10 carbon atoms; or alternatively from 1 to 5 carbon atoms. In an embodiment, the inert functional group is an etheryl group having the structure —$OR_{18}$ wherein $R_{18}$ represents an alkyl group. Applicable alkyl groups are generally described herein and may be utilized to further identify the alkyl group, $R_{18}$, of the etheryl group having the structure —$OR_{18}$.

$Y_1$ and $Y_2$ typically represent a structural bridge between two halves of a ligand or complex. $Y_1$ may be a bond between nitrogen group 30 and nitrogen group 40, a hydrocarbylene, a substituted hydrocarbylene, an alkylene, a substituted alkylene, or an inert functional group. $Y_2$ may be a bond between aromatic rings 120 and 130, a hydrocarbylene, substituted hydrocarbylene, an alkylene, a substituted alkylene, or an inert functional group. In an embodiment, the hydrocarbylene, substituted hydrocarbylene, alkylene, or substituted alkylene bridging group, $Y_1$ or $Y_2$, may have from 1 to 30 carbon atoms; alternatively, from 1 to 20 carbon atoms; alternatively, from 1 to 10 carbon atoms; or alternatively, from 1 to 5 carbon atoms. In further embodiments, the bridging group, $Y_1$ or $Y_2$, may be a bond. In some embodiments, the bridging group, $Y_1$ or $Y_2$, can be a methylene group ($CH_2$), an ethylene group ($C_2H_4$), a propylene group (—$CH_2CH_2CH_2$—), a —$CH(CH_3)CH_2$— group, —$C(CH_3)_2$— group, group (—$CH_2CH_2CH_2$—$CH_2$—), or a —$CH_2CH(CH_3)$—$CH_2$— group, or an inert functional group. In other embodiments, the bridging group, $Y_1$ or $Y_2$, can be a methylene group (—$CH_2$—), an ethylene group (—$CH_2CH_2$—), or a —$CH(CH_3)CH_2$-group; alternatively, a methylene group (—$CH_2$—); alternatively, an ethylene group (—$CH_2CH_2$—); alternatively, a propylene group (—$CH_2CH_2CH_2$—); alternatively, a —$CH(CH_3)CH_2$— group; alternatively, a —$C(CH_3)_2$— group; or alternatively, or a —$CH_2CH(CH_3)$—$CH_2$— group. In an embodiment, $Y_2$ may be link the two aromatic rings 120 and 130 at any carbon atom of the aromatic rings except the carbons atom to which $R_A$ and $R_B$ groups, or alternatively $R_A$, $R'_A$, $R_B$, and $R'_B$ groups are attached. In some embodiments, the two $R_{11}$ groups, or alternatively the $R_{11}$ and $R'_{11}$ groups, taken together form the structural bridge $Y_2$. In some embodiments, any two of $R_A$, $R'_A$, $R_6$, $R'_6$, $R_7$, $R'_7$, $R_B$, $R'_B$, $R_{11}$, $R'_{11}$, $R_C$, $R'_C$, $R_8$, $R'_8$, $R_9$, $R'_9$, $R_{10}$, $R'_{10}$, $R_D$, and $R'_D$, vicinal to one another, taken together may form a ring. In some embodiments, any of $R_A$, $R'_A$, $R_6$, $R'_6$, $R_7$, $R'_7$, $R_B$, $R'_B$, $R_{11}$, $R'_{11}$, $R_C$, $R'_C$, $R_8$, $R'_8$, $R_9$, $R'_9$, $R_{10}$, $R'_{10}$, $R_D$, and $R'_D$ vicinal to $Y_2$, taken together, may form a ring.

In other embodiments, when $R_A/R'_A$ is a primary carbon group, then none, one, or two of $R_B/R'_B$, $R_C/R'_C$, and $R_D/R'_D$ are primary carbon groups, secondary carbon groups, phenyl, substituted phenyl, or inert functional groups, and the remainder of $R_B/R'_B$, $R_C/R'_C$, and $R_D/R'_D$ are hydrogen or fluorine. In another embodiment, when $R_A/R'_A$ is a secondary carbon group, then none, one, or two of $R_B/R'_B$, $R_C/R'_C$, and $R_D/R'_D$ are primary carbon groups, secondary carbon groups, phenyl, substituted phenyl, or inert functional groups, and the remainder of $R_B/R'_B$, $R_C/R'_C$, and $R_D/R'_D$ are hydrogen or fluorine. In other embodiments, when $R_A/R'_A$ is a tertiary carbon group, then none or one of $R_B/R'_B$, $R_C/R'_C$, and $R_D/R'_D$ are tertiary, phenyl, or substituted phenyl, and the remainder are hydrogen or fluorine. In other embodiments, when $R_C/R'_C$ is a primary carbon group, then none, one, or two of $R_A/R'_A$, $R_B/R'_B$, and $R_D/R'_D$ are primary carbon groups, secondary carbon groups, phenyl, substituted phenyl, or inert functional groups, and the remainder of $R_A/R'_A$, $R_B/R'_B$, and $R_D/R'_D$ are hydrogen or fluorine. In other embodiments, when $R_C/R'_C$ is a secondary carbon group, then none, one, or two of $R_A/R'_A$, $R_B/R'_B$ and $R_D/R'_D$ are primary carbon groups, secondary carbon groups, phenyl, substituted phenyl, or inert functional groups, and the remainder of $R_A/R'_A$, $R_B/R'_B$, and $R_D/R'_D$ are hydrogen or fluorine. In other embodiments, when $R_C/R'_C$ is a tertiary carbon group, then none or one of $R_A/R'_A$, $R_B/R'_B$, and $R_D/R'_D$ are tertiary, phenyl, or substituted phenyl, and the remainder of $R_A/R'_A$, $R_B/R'_B$, and $R_D/R'_D$ are hydrogen or fluorine. Independent of the above limitations, $Y_1$ and $Y_2$ may be symmetric or asymmetric.

In an embodiment of HBC 15, $R_A$ and $R_B$ are hydrogen and $R_C$ and $R_D$ are each independently a primary or secondary carbon group; alternatively, $R_A$ and $R_B$ are hydrogen and $R_C$ and $R_D$ are each independently a primary carbon group; or alternatively, $R_A$ and $R_B$ are hydrogen and $R_C$ and $R_D$ are each independently methyl, ethyl, propyl, or isopropyl. In an embodiment, $R_A$ and $R_B$ are methyl and $R_C$ and $R_D$ are each independently a primary or secondary carbon group; alternately $R_A$ and $R_B$ are methyl and $R_C$ and $R_D$ are each independently a primary carbon group; or alternately, $R_A$ and $R_B$ are methyl and $R_C$ and $R_D$ are each independently methyl, ethyl, propyl, or isopropyl. In an embodiment, $R_C$ and $R_D$ are hydrogen and $R_A$ and $R_B$ are each independently a primary or secondary carbon group; alternatively, $R_C$ and $R_D$ are hydrogen and $R_A$ and $R_B$ are each independently a primary carbon group; or alternatively, $R_C$ and $R_D$ are hydrogen and $R_A$ and $R_B$ are each independently methyl, ethyl, propyl, or isopropyl. In an embodiment, $R_C$ and $R_D$ are methyl and $R_A$ and $R_B$ are each independently a primary or secondary carbon group; alternatively, $R_C$ and $R_D$ are methyl and $R_A$ and $R_B$ are each independently a primary carbon group; or alternatively, $R_C$ and $R_D$ are methyl and $R_A$ and $R_B$ are each independently methyl, ethyl, propyl, or isopropyl. In an embodiment, $R_A$ and $R_D$ are hydrogen and $R_B$ and $R_C$ are each independently a primary or secondary carbon group; alternatively $R_A$ and $R_D$ are hydrogen and $R_B$ and $R_C$ are each independently a primary carbon group; alternatively, $R_A$ and $R_D$ are hydrogen and $R_B$ and $R_C$ are each independently methyl, ethyl, propyl, or isopropyl; alternatively, $R_A$ and $R_D$ are hydrogen and $R_B$ and $R_C$ are methyl; or alternatively, $R_A$ and $R_D$ are hydrogen and $R_B$ and $R_C$ are ethyl. In an embodiment, $R_A$ and $R_D$ are methyl and $R_B$ and $R_C$ are each independently a primary or secondary carbon group; alternatively, $R_A$ and $R_D$ are methyl and $R_B$ and $R_C$ are each independently a primary carbon group; or alternatively, $R_A$ and $R_D$ are methyl and $R_B$ and $R_C$ are each independently methyl, ethyl, propyl, or isopropyl.

In some embodiments, $R_A$, $R_B$, $R'_A$, and $R'_B$ are selected such that each M has an asymmetric environment with respect to the ortho positions on rings 100 and 120, and/or 130 and 150. In further embodiments, $R_A$, $R_B$, $R'_A$, and $R'_B$ are selected such that each M has an asymmetric environment with respect to the ortho positions on rings 100 and 120, and/or 130 and 150 in HBC 8.

In an embodiment, a HBC having a chemical structure such as those shown in HBC 1-10, may have the pendant groups as defined above, except that both M and M' are iron; or alternatively, cobalt. In another embodiment, selection of M and M' affects selection of $R_A$, $R_B$, $R_C$, $R_D$, W, and $Y_1$.

In an embodiment a HBC having a chemical structure such as shown in HBC 9, may have the pendant groups as defined herein, with the following exceptions:

$R_1$, $R_2$, and $R_3$ are hydrogen;
$R_4$ and $R_5$ are methyl or hydrogen;
$R_6$, $R_7$, $R_8$, $R_9$, and $R_{10}$ are hydrogen;
$R_A$, $R_B$, $R_C$, and $R_D$ are each independently hydrogen methyl, ethyl, propyl, or isopropyl; and
$Y_2$ represents the structural bridge.

In another embodiment a HBC having a chemical structure such as shown in HBC 9, may have the pendant groups as defined herein, with the following exceptions:

$R_1$, $R_2$, and $R_3$ are hydrogen;
$R_4$ and $R_5$ are methyl;
$R_6$, $R_7$, $R_8$, $R_9$, and $R_{10}$ are hydrogen;
$R_A$, $R_B$, $R_C$, and $R_D$ are each independently hydrogen methyl, ethyl, propyl, or isopropyl; and
$Y_2$ represents the structural bridge.

Generally, the metal compound(s), $M-X_n$ and/or $M'-X'_n$, may be any metal compound capable of complexing with the hexadentate ligand. In an embodiment, the metal of the metal compound, M and/or M', may be a transition metal. In some embodiments, the metal of the metal compound, M and/or M', may be a Group VB, VIB, or VIII (the group designations are that of the CAS version of the Periodic Table). In further embodiments, the metal of the metal compound(s), M and/or M', may be cobalt, iron, chromium, vanadium, or mixtures thereof. In other embodiments, the metal of the metal compounds, M and/or M', may be iron or cobalt. In an embodiment, the metal of the metal compound(s), M and/or M', may be iron; alternatively, cobalt. In an embodiment, the metal of the metal compound(s), M and/or M', have an oxidation state of +1, +2 or +3; alternatively +2 or +3; or alternatively +2.

X and X' of the metal compound(s) may independently be any anion. In an embodiment, X and X' are independently a halide, carboxylate, acetonate, alkoxide, phenoxide, nitrate, sulfate, phosphate, or chlorate. In some embodiments, X and X' can independently be a halide, carboxylate, or acetonate. In other embodiments, X and X' can independently be a halide; alternatively, a carboxylate; or alternatively, acetonate.

The number of X groups (or X' groups), n, is such that the total number of negative charges on the total number X or X' anion(s) equals the oxidation state of M or M' respectively. In some embodiments, n is 1, 2, or 3 and the total number of negative charges on X or X' is equal to the oxidation state of M or M', respectively. In other embodiments, n may be 2 or 3; alternatively, 2; or alternatively 3.

In an embodiment, the halide anion can be fluoride, chloride, bromide, iodide, or combinations thereof; alternatively, chloride, bromide, iodide, or combinations thereof. In other embodiments, the halide anion can be chloride; alternatively, bromide; or alternatively, iodide. In some embodiments, the metal compound(s) may be a metal halide. In other embodiments, the metal compound may be an iron(II) halide or iron(III) halide; alternatively, a cobalt(II) halide or cobalt(III) halide; or alternatively, a chromium(II) halide or chromium (III) halide.

In carboxylate, acetonate, alkoxide or phenoxide embodiments, the carboxylate, acetonate, alkoxide, or phenoxide can be any $C_1$ to $C_{20}$ carboxylate, acetonate, alkoxide, or phenoxide; or alternatively, any $C_1$ to $C_{10}$ carboxylate, acetonate, alkoxide, or phenoxide. In some embodiments, X and/or X', can independently be a $C_1$ to $C_{10}$ acetonate; alternatively, a $C_1$ to $C_{10}$ carboxylate; alternatively, a $C_1$ to $C_{10}$ alkoxide; or alternatively, a $C_1$ to $C_{10}$ phenoxide. In other embodiments, X and/or X', can independently be acetylacetonate; alternatively, acetate; alternatively, 2-ethylhexanoate; or alternatively, triflate.

In an embodiment, the metal compound(s) can be chromium(II) chloride, chromium(III) chloride, chromium(II) fluoride, chromium(III) fluoride, chromium (II) bromide, chromium(III) bromide, chromium(II) iodide, chromium(III) iodide, chromium(II) acetate, chromium (III) acetate, chromium(III) acetylacetonate, chromium(II) 2-ethylhexanoate, chromium (II) triflate, chromium(III) nitrate, iron(II) chloride, iron(III) chloride, iron(II) fluoride, iron(III) fluoride, iron (II) bromide, iron(III) bromide, iron(II) iodide, iron(III) iodide, iron(II) acetate, iron (III) acetate, iron(II) acetylacetonate, iron(III) acetylacetonate, iron(II) 2-ethylhexanoate, iron (II) triflate, iron(III) nitrate, cobalt(II) chloride, cobalt (III) chloride, cobalt(II) fluoride, cobalt(III) fluoride, cobalt (II) bromide, cobalt(III) bromide, cobalt(II) iodide, cobalt (III) iodide, cobalt(II) acetate, cobalt (III) acetate, cobalt(II) acetylacetonate, cobalt(II) benzoylacetonate, cobalt(III) acetylacetonate, cobalt(II) 2-ethylhexanoate, cobalt (II) triflate, cobalt(III) nitrate, vanadium (III) chloride, vanadium (II) chloride, vanadium(III) chloride tetrahydrofuran complex, vanadium (III) iodide, manganese(II) acetate, manganese(II) acetylacetonate, manganese(II) bromide, manganese (II) chloride, manganese(II) fluoride, manganese(III) fluoride, manganese(II) iodide, or any combination thereof. In some embodiments, the metal compound can be chromium (II) chloride, chromium(III) chloride, chromium(II) acetate, chromium (III) acetate, chromium(III) acetylacetonate, iron (II) chloride, iron(III) chloride, iron(II) acetate, iron (III) acetate, iron(II) acetylacetonate, iron(III) acetylacetonate, cobalt(II) chloride, cobalt(III) chloride, cobalt(II) acetate, cobalt (III) acetate, or cobalt(II) acetylacetonate, or any combination thereof. In other embodiments, the metal compound can be chromium(II) chloride, chromium(III) acetylacetonate, iron(II) chloride, iron(II) acetylacetonate, iron(III) acetylacetonate, cobalt(II) chloride, cobalt(II) acetylacetonate, or any combination thereof. In further embodiments, the metal compound can be chromium(II) chloride; alternatively, chromium(III) acetylacetonate; alternatively, iron(II) chloride; alternatively, iron(II) acetylacetonate; alternatively, cobalt(II) chloride; or alternatively, cobalt(II) acetylacetonate.

HBCs of the type disclosed herein may be prepared as known to one of ordinary skill in the art. Such methods are described for example in U.S. patent application Ser. No. 11/009,916 entitled "Methods for producing a Hexadentate Bimetallic Complex" incorporated by reference herein in its entirety.

Minimally, the catalyst system comprises the catalyst. In an embodiment, the catalyst may be a hexadentate bimetallic complex. In some embodiments, the catalyst system comprises, or consists essentially of, a catalyst and a cocatalyst. In an embodiment, the catalyst system comprises, or consists essentially of, a hexadentate bimetallic complex and a cocatalyst. The hexadentate bimetallic complex and the cocatalyst are independently described herein and may be utilized in any combination to describe the catalyst system.

Generally, the cocatalyst can be any organometallic compound capable of activating the HBC described herein. In an embodiment, the cocatalyst comprises a metal alkyl or metal hydride species. In another embodiment, the cocatalyst comprises one or more Lewis acids, or a combination of one or more Lewis acids and one or more alkylating agents. In an embodiment, the cocatalyst can be selected from the group consisting of organoaluminum compounds, organoboron compounds, organomagnesium compounds, organozinc compounds, organolithium compounds, or mixtures thereof. In some embodiments, the cocatalyst can be an organoaluminum compound. Applicable organoaluminum compounds can include trialkyl-aluminums, alkylaluminum halides, alumoxanes, or mixtures thereof. In some embodiments, the organoaluminum compound can comprise, or consist essentially of, one or more trialkylaluminums; alternatively, alkylaluminum halides; or alternatively, alumoxanes. In yet other embodiments, the cocatalyst consists of one or more alumoxanes. The metal alkyl can have any number of carbon atoms. However, due to commercial availability and ease of use, the metal alkyl will usually comprise less than about 70 carbon atoms per metal alkyl molecule and alternatively less than about 20 carbon atoms per molecule.

Suitable cocatalysts include, but are not limited to, n-butyllithium, s-butyllithium, t-butyllithium, diethylmagnesium, dibutylmagnesium, diethylzinc, triethylaluminum, trimethylaluminum, tripropylaluminum, tributylaluminum, triisobutylaluminum, tri-n-hexylaluminum, tri-n-octylaluminum, diethylaluminum ethoxide, diethylaluminum phenoxide, ethylaluminum dichloride, diethylaluminum chloride, diethylaluminum bromide, diethylaluminum sesquichloride, diisobutylaluminum chloride, ethylaluminum sesquichloride, diethylaluminum bromide, diethylaluminum iodide, ethylaluminumethoxychloride, and mixtures thereof. In an embodiment, the alkylaluminum compound may be triethylaluminum.

In an embodiment, the cocatalyst may comprise at least one alkylaluminum compound. In some embodiments, the cocatalyst can be a trialkylaluminum compound. Suitable organoaluminum cocatalysts can include, but are not limited to, trimethylaluminum, triethylaluminum, tripropylaluminum, tri-n-butylaluminum, tri-iso-butylaluminum, tri-n-hexylaluminum, tri-n-octylaluminum, diethylaluminumchloride, diethylaluminumbromide, diethylaluminumethoxide, diethylaluminum phenoxide, ethylaluminumethoxychloride, diethylaluminum cyanide, ethylaluminum dichloride, diethylaluminum chloride, diethylaluminum bromide, ethylaluminum sesquichloride, diisobutylaluminum chloride, methylaluminoxane (MAO), modified methylaluminoxane (MMAO), ethylaluminoxanes, isobutyl alumoxanes, t-butyl alumoxanes, and mixtures thereof. In other embodiments, the alumoxane can include methylalumoxane (MAO), modified methylalumoxane (MMAO), isobutyl alumoxanes, t-butyl alumoxanes, or mixtures thereof. In other embodiments, the cocatalyst can comprise methylalumoxane, modified methylalumoxane, or mixtures thereof. In yet other embodiments, the cocatalyst can comprise methylalumoxane; alternatively, modified methylalumoxane; isobutylalumoxane (IBAO); or alternatively, a partially hydrolyzed trialkylaluminum.

Generally, the molar ratio of the metal of the cocatalyst to the metal of the catalyst (e.g. hexadentate bimetallic complex) can be any ratio which produces an active catalyst system. In an embodiment, the molar ratio of the metal of the cocatalyst to the metal of the catalyst (e.g. hexadentate bimetallic complex) is greater than 1:1; alternatively, greater than 10:1; alternatively, greater than 25:1; or alternatively, greater than 50:1. In some embodiments, the molar ratio of metal in the cocatalyst to metal in the catalyst (e.g. hexadentate bimetallic complex) ranges from 1:1 to 10,000:1; alternatively 10:1 to 3,000:1; or alternatively 50:1 to 2,000. In some embodiments wherein the metal compound of the catalyst (e.g. hexadentate bimetallic complex) is iron and the cocatalyst is one or more alkylaluminum compounds (e.g. trialkylaluminum, alkylaluminum halide or alumoxane), the molar ratio of aluminum to iron can range from 1:1 to 10,000:1; alternatively, from 10:1 to 3,000:1; or alternatively, from 50:1 to 2,000:1. In some embodiments, the metal compound of the catalyst (e.g. hexadentate bimetallic complex) is cobalt and the cocatalyst is one or more alkylaluminum compounds (e.g. trialkylaluminum, alkylaluminum halide or alumoxane), the molar ratio of aluminum to cobalt can range from 1:1 to 10,000:1; alternatively, from 10:1 to 3,000:1; or alternatively, from 50:1 to 2,000:1.

In an embodiment, the catalyst, cocatalyst, and/or catalyst system can be found in a composition comprising a solvent or diluent. In some embodiments, a composition comprising the catalyst may comprise, or consist essentially of the catalyst and a solvent or diluent. In some embodiments, a composition comprising the cocatalyst may comprise, or consist essentially of the cocatalyst and a solvent or diluent. In some embodiments, a composition comprising the catalyst system may comprise, or consist essentially of the catalyst system and a solvent or diluent. In some embodiments, the composition comprising the catalyst may be substantially devoid of a solvent or diluent.

The solvent or diluent may be a hydrocarbon solvent, a halogenated hydrocarbon solvent, or combinations thereof. Generally, the catalyst system solvent or diluent can comprise a $C_4$ to $C_{20}$ hydrocarbon; alternatively, a $C_4$ to $C_{10}$ hydrocarbon; alternatively, $C_1$ to $C_{15}$ halogenated hydrocarbon; or alternatively, $C_1$ to $C_{10}$ halogenated hydrocarbon. The hydrocarbon solvent or diluent can be a saturated hydrocarbon, an aromatic hydrocarbon, or an olefinic hydrocarbon. In an embodiment, the saturated hydrocarbon solvent or diluent may comprise butane, isobutane, pentane, n-hexane, hexanes, cyclohexane, n-heptane, n-octane, or mixtures thereof. In some embodiments, the aromatic solvent or diluent can be a $C_6$ to $C_{20}$ aromatic compound. Suitable aromatic hydrocarbons can include benzene, toluene, mixed xylenes, ortho-xylene, meta-xylene, para-xylene, ethylbenzene, or mixtures thereof. Suitable halogenated catalyst solvents or diluents can include, carbon tetrachloride, chloroform, methylene chloride, dichloroethane, trichloroethane, chlorobenzene, or dichlorobenzene, or mixtures thereof.

The catalyst system components disclosed herein may be contacted to form an catalyst system. The amount of each catalyst system component can be any amount which forms an active catalyst system. Generally, a molar excess of the cocatalyst is used. The catalyst system may be individually prepared prior to contact with the olefin. As such, in an embodiment, the composition comprising the catalyst and the cocatalyst is contacted with the olefin(s). In other embodiments, all or some of the components of the catalyst system may be separately contacted with the olefin and the catalyst system formed in a composition comprising the olefin. In an embodiment, the catalyst and the cocatalyst are separately contacted with the olefin. In some embodiments, a composition comprising, or consisting essentially of, the catalyst and an optional a solvent or diluent is contacted with a composition comprising the olefin and the cocatalyst; alternatively, a composition comprising, or consisting essentially of, the cocatalyst and an optional solvent or diluent is contacted with a composition comprising the olefin and catalyst.

In the various embodiments disclosed herein, contacting of catalyst components may occur in one or more contact zones. A contact zone is a zone in which the components are commingled and/or combined, and thereby contacted. The contact zone may be disposed in a vessel, e.g. a storage tank, tote, container, mixing vessel, reactor, etc.; a length of pipe, e.g. a tee, inlet, injection port, or header for combining component feed lines into a common line; or any other suitable apparatus for bringing the components into contact. As used herein, the terms contacted and combined refer to any addition sequence, order, or concentration for contacting or combining two or more catalyst components. In some embodiments, contacting of components may occur in one or more upstream contact zone(s) prior to further contacting with other catalyst component(s) in one or more downstream contact zone(s). Where a plurality of contact zones are employed, contacting may occur simultaneously across the contact zones, sequentially across the contact zones, or both, as is suitable for a given embodiment. Contacting may be carried out in a batch or continuous process, as is suitable for a given embodiment.

In embodiments utilizing a vessel for contacting the components, the components may be optionally mixed by a mixer disposed in the vessel and the formed mixture may then be removed for subsequent processing. In embodiments utilizing a tee or other means for combing lines such as a header, an optional in-line mixer may be placed in the commingled catalyst feed line to ensure that adequate contacting of the combined components takes place, and the mixture is thus formed as it passes through the commingled feed line.

As used herein, a composition comprising a catalyst system component includes the catalyst system component alone or in combination with one or more additional compounds, solvents, or both. None, some, or all of the contacting steps may be carried out in the presence of a solvent (sometimes referred to as an optional solvent), which may be introduced to a contact zone via inclusion with one or more compositions comprising a catalyst system component or may be introduced separately to a contact zone, for example in a solvent line or as an initial charge to a contact zone.

Contacting of the catalyst system components can be done under any conditions sufficient to thoroughly contact the components. Typically, contacting is performed in an inert atmosphere, such as, for example, nitrogen and/or argon.

Generally, the olefin utilized in the dimerization or isomerization processes described herein may be described as having a combination of features such as carbon number, the olefin type (e.g. linear, branched, alpha or other), and the percentage of a olefin type, among other properties. These features are described independently herein and may be used in any combination to describe the olefin utilized for the dimerization or isomerization processes described herein.

In an embodiment, the olefin may comprise, or consist essentially of, olefins having at least 3 carbon atoms; alternatively, at least 4 carbon atoms; alternatively, at least 5 carbon atoms; alternatively, least 6 carbon atoms; or alternatively, at least 10 carbon atoms. In some embodiments, the olefin may comprise, or consist essentially of, olefins having from 3 to 60 carbon atoms; alternatively, olefins having from 4 to 60 carbon atoms; alternatively, from 5 to 60 carbon atoms; alternatively, from 5 to 30 carbon atoms; alternatively, from 5 to 20 carbon atoms; alternatively, from 6 to 60 carbon atoms carbon atoms; alternatively, from 6 to 30 carbon atoms; alternatively, from 6 to 20; alternatively, from 10 to 60 carbon atoms; alternatively, from 10 to 30 carbon atoms; or alternatively, from 10 to 20 carbon atoms.

In an embodiment, the olefin may comprise, or consist essentially of, alpha olefins. In some embodiments, the olefin may comprise, or consist essentially of, linear alpha olefins. In other embodiments the olefin may comprise, or consist essentially of, normal alpha olefins. In some embodiments, the alpha olefin may be a hydrocarbon alpha olefin. In some embodiments, the linear alpha olefin may be a linear hydrocarbon alpha olefin. In some embodiments, the hydrocarbon alpha olefin may be a mono-olefinic hydrocarbon alpha olefin. In some embodiments, the linear alpha olefin may be a linear mono-olefinic alpha olefin.

In an embodiment, the olefin can comprise greater than 30, 45, 60, 75, 90, or 95 mole percent alpha olefins, linear alpha olefins, or normal alpha olefins. In other embodiments, the olefin can comprise from 50 to 99, from 55 to 98, from 60 to 97, or from 65 to 95 mole percent alpha olefins, linear alpha olefins, or normal alpha olefins. The weight percentages of the alpha olefins, linear alpha olefins, and normal alpha olefins also apply to any other types of alpha olefins, and linear alpha olefins (e.g. mono-olefinic, aliphatic, hydrocarbon, and acyclic, among others) described herein. Non-limiting examples of olefins which may be utilized either individually or in any combination include propene, 1-butene, 1-pentene, 1-hexene, 1-heptene, 1-octene, 1-decene, 1-dodecene, 1-tetradecene, 1-hexadecene, and 1-octadecene.

The catalyst and catalyst systems described in the present application can be employed in the dimerization of olefins. In such embodiments, the catalyst or catalyst system may be referred to as a dimerization catalyst or dimerization catalyst system, respectively. In other embodiments, the catalyst and catalyst systems described in the present application can be employed in the isomerization of olefins. In such embodiments, the catalyst or catalyst system may be referred to as an isomerization catalyst or isomerization catalyst system, respectively.

The dimerization process can be carried out by contacting the catalyst or catalyst system with one or more olefins and dimerizing the olefin(s) under reaction conditions suitable for the dimerization of olefins. The isomerization process can be carried out by contacting the catalyst or catalyst system with one or more olefins and dimerizing the olefin(s) under reaction conditions suitable for the isomerization of olefins. Generally, the olefins for the dimerization or isomerization process are the same and will be described generally as olefins. When referenced with the dimerization process the olefin(s) may be referred to as olefin(s) or olefin monomer(s).

In an aspect, the process for dimerizing olefins comprises: a) contacting i) an olefin and ii) a catalyst system; and b) dimerizing the olefin in a reaction zone under conditions effective to dimerize the olefin to form a reaction zone effluent comprising olefin oligomers including olefin dimers. In an embodiment, the process for dimerizing olefin comprises: a) contacting i) an olefin, ii) a catalyst, and iii) a cocatalyst; and b) dimerizing the olefin in a reaction zone under conditions effect to dimerize the olefin to form a reaction zone effluent comprising olefin oligomers including olefin dimers. The olefin, catalyst, cocatalyst, and dimerization reaction conditions, are independently described herein and may be utilized in any combination to further describe the process for dimerizing olefins. For example, in some non-limiting embodiments, the olefin may be any alpha olefin described herein, the catalyst may be any hexadentate bimetallic complex described herein, and the cocatalyst may be any cocatalyst described herein. When the olefin is an alpha olefin, the olefin oligomers and olefin dimers may be, but need not necessarily be, called alpha olefin oligomers and alpha olefin dimers, respectively. The same logic applies for other olefins (e.g. linear alpha olefin, or normal alpha olefins, among others).

The conditions effective to form the olefin dimer are described herein and may be utilized to further describe the process for dimerizing olefins. The process for dimerizing olefins may produce a reaction zone effluent having particular compositional elements, for example olefin oligomers and olefin dimers among others. The compositional elements of the reaction zone effluent are described herein and may be utilized to further describe the process for dimerizing olefins.

Generally, the dimerization process produces a reaction zone effluent containing significant quantities of olefin dimers (e.g. alpha olefin dimers). As used herein, dimer refers to a molecule of intermediate mass (relative to, for example, a polymer), the structure of which comprises two units derived from molecules of lower relative mass, e.g. an olefin. While the intent of the dimerization process is to produce olefin dimers, it should be noted that the olefin dimerization, while producing a quantities of olefin dimers, may also produce some quantities of other olefin oligomers (e.g. trimers, tetramers, etc . . . ). Consequently, the reaction zone effluent of the dimerization process may be described as containing a particular percentage of olefin dimers in relation to the total quantity of olefin oligomers formed. The reaction zone effluent of the dimerization process may also be described as having attained a conversion of the olefin to olefin oligomers. The conversion of the olefin to olefin oligomers and the weight percent of olefin dimers in relation to the total quantity of olefin oligomers formed are described independently and may be utilized in any combination to describe the reaction zone effluent.

In an embodiment, the dimerization process produces a reaction zone effluent wherein greater than 20, 30, 40, or 50 weight percent of the olefin has been converted to olefin oligomers. In other embodiments, the dimerization process produces a reaction zone effluent wherein from 20 to 95, from 30 to 85, from 40 to 80, or from 50 to 75 weight percent olefin has been converted to olefin oligomers. Independent of the olefin conversion, the reaction zone effluent comprises olefin oligomers and the olefin oligomers may comprise greater than 60, 70, 75, or 80 weight percent olefin dimers. In other embodiments, the olefin oligomers, of reaction zone effluent, may comprise from 60 to 99, from 70 to 98, from 75 to 95, or from 80 to 95 weight percent olefin dimers.

Independent of the olefin monomer conversion and the percentage of olefin dimers present in the olefin oligomer product of the reaction zone effluent, the dimers produced by dimerization process may described as having features such as the weight percent dimers formed, weight percent of linear dimers found in the dimer product, the weight percent of branched dimers found in the dimer product, and the weight percent of methyl branched dimers found in the dimer product, among other properties. These features of the olefin dimers are independently described herein and may be used in any combination to describe the reaction zone effluent and/or the dimers within the reaction zone effluent.

The dimers formed by olefin dimerization process may comprises at least 30 mole percent linear dimers; alternatively, at least about 50 mole percent linear dimers; or alternatively, at least about 60 mole percent linear dimers. In some embodiments, the olefin dimers formed from the dimerization of the alpha olefins comprises from 30 to 99 mole percent linear dimers; alternatively from 50 to 95 mole percent linear dimers, alternatively form 60 to 90 mole percent linear dimers. The weight percent linear dimers formed by the dimerization process is based on the weight of dimers in the reaction product, and not the total weight of the olefin oligomers formed by the dimerization process.

In an embodiment, less than 70, 50, or 40 weight percent of the dimers are branched. In other embodiments, from 1 to 60, from 5 to 50, or from 10 to 40 weight percent of the dimers are branched. The weight percent branched dimers formed by the dimerization process is based on the weight of dimers in the reaction product, and not the total weight of the olefin oligomers formed by the dimerization process. In some particular embodiments, the branched dimer may be an olefin dimer having a methyl branch. In other embodiments, the branched dimer may be an olefin dimer having at a methyl branch a carbon atom one or two carbon atoms away from the carbon-carbon double bond. In some embodiments, the dimers may comprise less than 70, 50, or 40 weight percent dimers having a methyl branch at a carbon atom one or two carbon atoms away from the carbon-carbon double bond. In other embodiments, the dimers may comprise from 1 to 60, from 5 to 50, or from 10 to 40 weight percent dimers having a methyl branch a carbon atom one or two carbon atoms away from the carbon-carbon double bond.

In some embodiments, the process for dimerizing olefins produces dimers which are internal olefins.

In a particular embodiment, the dimerization may produce highly linear dimers if one utilizes a cobalt hexadentate bimetallic complex. In an embodiment, the particular process for dimerizing olefins comprises: a) contacting i) an olefin and ii) a catalyst system comprising a hexadentate bimetallic complex comprising a cobalt compound; and b) dimerizing the olefin in a reaction zone under conditions effective to dimerize the olefin to form a reaction zone effluent comprising olefin oligomers including olefin dimers. In another embodiment, the particular process for dimerizing olefin comprises: a) contacting i) an olefin, ii) a hexadentate bimetallic complex comprising a cobalt compound, and iii) a cocatalyst; and b) dimerizing the olefin in a reaction zone under conditions effective to dimerize the olefin to form a reaction zone effluent comprising olefin oligomers including olefin dimers. The olefin, hexadentate bimetallic complex comprising a cobalt compound, cocatalyst, and dimerization reaction conditions, are independently described herein and may be utilized in any combination to further describe the process for dimerizing olefins. For example, in some non-limiting embodiments, the olefin may be any alpha olefin described herein, the catalyst may be any hexadentate bimetallic complex comprising a cobalt compound described herein, and the cocatalyst may be any cocatalyst described herein. When the olefin is an alpha olefin, the olefin oligomers and olefin dimers may be, but need not necessarily be, called alpha olefin oligomers and alpha olefin dimers, respectively. The same logic applies for other olefins (e.g. linear alpha olefin, or normal alpha olefins, among others). In a further embodiment, the particular process for dimerizing olefins comprises: a) contacting (i) an alpha olefin having at least 3 carbon atoms, (ii) a hexadentate bimetallic complex comprising a cobalt compound, and (iii) a cocatalyst; and b) dimerizing the alpha olefin in a reaction zone at conditions effective to dimerize an alpha olefin to form a reaction zone effluent comprising oligomers including dimers.

In an embodiment, the alpha olefin dimerization process utilizing a cobalt hexadentate bimetallic complex may produce a reaction zone effluent wherein greater than 20, 30, 40, or 50 weight percent of the alpha olefin has been converted to oligomers. In some embodiments, the alpha olefin dimerization process utilizing a cobalt hexadentate bimetallic complex may produce a reaction zone effluent wherein from 20 to 90, from 30 to 85, from 40 to 80, or from 50 to 75 weight percent of the alpha olefin has been converted to oligomers. Independent of the olefin conversion, the reaction zone effluent of the alpha olefin dimerization process utilizing a cobalt hexadentate bimetallic complex comprises oligomers and the oligomers may comprise greater than 30, 40, 50, or 60 weight percent dimers. In other embodiments, the oligomers, of reaction zone effluent of the alpha olefin dimerization process utilizing a cobalt hexadentate bimetallic complex, may comprise from 30 to 95, from 40 to 90, from 50 to 85, or from 60 to 80 weight percent dimers.

The dimers from the dimerization of the alpha olefins using a cobalt hexadentate bimetallic complex may comprises at least 85 mole percent linear dimers; alternatively, at least about 90 mole percent linear dimers; or alternatively, at least about 95 mole percent linear dimers. In some embodiments, the olefin dimers formed from the dimerization of the alpha olefins using a cobalt hexadentate bimetallic complex may comprise from 85 to 99.9 mole percent linear dimers; alternatively from 90 to 99.9 mole percent linear dimers, alternatively form 95 to 99.9 mole percent linear dimers. The weight percent linear dimers formed by the dimerization of the alpha olefins using a cobalt hexadentate bimetallic complex is based on the weight of dimers in the reaction product, and not the total weight of the olefin oligomers formed by the dimerization process.

Generally, the reaction conditions effective to dimerize olefins may include reaction temperature, reaction time, and reaction pressure. It is known in the art that the reaction time may be affected by the reaction temperature of the dimerization. Additionally, it is known in the art that the reaction time and/or temperature of the dimerization may vary depending on the identity of the dimerization catalyst system employed. Furthermore, the compositional elements of the reaction zone effluent such as weight percent olefin oligomer and/or weight percent olefin dimer along with the olefin conversion may be affected by the identity of the dimerization catalyst system, reaction time, and reaction temperature. Consequently, the reaction conditions for the process for dimerizing olefins are independently described herein and may be utilized in any combination to describe reaction conditions utilized to dimerize olefin and/or to produce a reaction zone effluent having particular compositional elements.

In an embodiment, the reaction temperature for the olefin dimerization process ranges from 0 to 150 degrees Celsius. In another embodiment, the reaction temperature of the olefin dimerization process ranges from 10 to 100 degrees Celsius; alternatively, ranges from 15 to 70 degrees Celsius; alternatively, ranges from 20 to 65 degrees Celsius; or alternatively, ranges from 25 to 60 degrees Celsius.

In an embodiment, the reaction time for the olefin dimerization process may be greater than 1 minute; alternatively, greater than 5 minutes; alternatively greater than 15 minutes; or alternatively, greater than 30 minutes; or alternatively greater than 1 hour. In other embodiments, the reaction time for the olefin dimerization process may range from 1 minute to 48 hours; alternatively, range from 2 minutes to 24 hours; alternatively, range from 5 minutes to 12 hours; or alternatively, range from 10 minutes to 6 hours.

In an embodiment, the reactor pressure for the olefin dimerization process may be chosen by one of ordinary skill in the art to be compatible with the user desired processes and equipment. For example, the reaction pressure may be maintained at atmospheric pressure. In other embodiments, the reaction pressure may be maintained above atmospheric pressure. In further embodiments, the reaction pressure for the olefin dimerization process may range from atmospheric pressure to 3000 psig; alternatively, from atmospheric pressure to 2000 psig; or alternatively from atmospheric pressure to 1000 psig. In particular embodiments, the reaction pressure for the olefin dimerization process may be maintained at a pressure greater than or equal to a pressure that maintains olefin in a liquid state at the reaction temperature employed. In some other embodiments, the reaction pressure for the olefin dimerization process may be maintained at a pressure ranging from a pressure that maintains olefin in a liquid state at the reaction temperature employed to 3000, 2000, or 1000 psig.

In an aspect, the process for isomerizing olefins comprises: a) contacting i) an olefin, ii) a catalyst system; and b) isomerizing the olefins in a reaction zone under conditions effective to isomerize the olefin to form a reaction zone effluent comprising isomerized olefins. In an embodiment, the process for isomerizing olefins comprises: a) contacting i) an olefin, ii) a catalyst, and iii) a cocatalyst; and b) isomerizing the olefins under conditions effective to isomerize the olefin to form a reaction zone effluent comprising isomerized olefins. The olefin, catalyst, cocatalyst, and isomerization reaction conditions, are independently described herein and may be utilized in any combination to further describe the process for isomerizing olefins. For example, in some non-limiting embodiments, the olefin may be any alpha olefin described herein, the catalyst may be any hexadentate bimetallic complex described herein, and the cocatalyst may be any cocatalyst described herein. When the olefin is an alpha olefin, the isomerized olefin may be, but need not necessarily be, called an isomerized alpha olefin. The same logic applies for other olefins (e.g. linear alpha olefin, or normal alpha olefins, among others).

The conditions effective to isomerize the olefin are described herein and may be utilized to further describe the process for isomerizing olefins. The process for isomerizing olefins may produce a reaction zone effluent having a particular compositional element(s). The compositional elements of the reaction zone effluent are described herein and may be utilized to further describe the process for dimerizing olefins.

Generally, the isomerization process produces a reaction zone effluent containing significant quantities of olefin in which the bond of the olefin has been isomerized. As used herein, an isomerized olefin refers to an olefin in which a double bond has been moved to a position other than its original position and has the same number of carbon atoms as the original olefin. Isomerized olefins may include olefins in which skeletal rearrangements of the olefin backbone have occurred. Linear olefin isomerization refers to an olefin isomerization wherein there is substantially no skeletal isomerization (i.e. less than 5 weight percent of the isomerized olefin has been skeletally isomerized).

While the intent of the isomerization process is to produce isomerized olefin, it should be noted that the olefin isomerization process may produce some quantities of olefin oligomers and may not convert all of the original olefin to isomerized olefins and/or olefin oligomers. Consequently, the reaction zone effluent of the olefin isomerization process may be described as containing a particular weight percent of olefin oligomers, a particular weight percent of olefin (i.e. original olefin), and/or a particular weight percent of isomerized olefins in relation to the quantity of olefin (i.e. original olefin) subjected to the isomerization process. The weight percent of olefin oligomers, the weight percent of olefin, and the weight percent of isomerized olefin in the reaction zone effluent of the olefin isomerization process are independently described herein and may be utilized in any combination to describe the reaction zone effluent of the olefin isomerization process.

In an embodiment, the reaction zone effluent of the olefin isomerization process comprises less than 30, 20, or 10 weight percent olefin oligomers (e.g. dimer, trimers, tetramers, etc . . . ). In an embodiment, the reaction zone effluent of the olefin isomerization process comprises less that 30, 20, 10, or 5 weight percent of the olefin isomer charged to the olefin isomerization alpha olefin. In an embodiment, the reaction zone effluent of the olefin isomerization process comprises greater than 60, 70, 80, or 90 weight percent isomerized olefin.

In particular embodiments, the olefin isomerization process may be applied to any alpha olefin described herein (e.g. general alpha olefins, linear alpha olefin, and normal alpha olefin, among others) and may be described as an alpha olefin isomerization process. In alpha olefin isomerization process embodiments, the isomerized alpha olefin of the reaction zone effluent may be described as having features such as the weight percent of 2-olefins and/or the weight percent of 2- and 3-olefins. The weight percent of 2-olefin and the weight percent of 2- and 3-olefins present in the isomerized olefins of the reaction zone effluent are independently described herein and may be utilized in any combination to describe the isomerized olefins of the reaction zone effluent. In an embodiment, at least about 70, 80, 90, or 95 weight percent of the isomerized alpha olefins may be 2-olefins and 3-olefins. In other embodiments, at least about 60, 70, 80, 90, or 95 weight percent of the isomerized alpha olefins may be 2-olefins.

Generally, the reaction conditions effective to isomerize olefins may include reaction temperature, reaction time, and reaction pressure. It is known in the art that the reaction time may be affected by the reaction temperature of the isomerization. Additionally, it is known in the art that the reaction time and/or temperature of the isomerization may vary depending on the identity of isomerization catalyst system employed. Furthermore, the compositional elements of the reaction zone effluent such as weight percent olefin oligomer, weight percent olefin, and/or weight percent isomerized olefin may be affected by the identity of the isomerization catalyst system, reaction time, and reaction temperature. Consequently, the reaction conditions for the process for isomerizing olefins are independently described herein and may be utilized in any combination to describe reaction conditions utilized to isomerize the olefin and/or to produce a reaction zone effluent having particular compositional elements.

In an embodiment, the reaction temperature for the olefin isomerization may range from 0 to 70 degrees Celsius. In another embodiment, the reaction temperature for the olefin isomerization may range from 0 to 60 degrees Celsius; or alternatively, ranges from 5 to 50 degrees Celsius; or alternatively, ranges from 5 to 40 degrees Celsius.

In an embodiment, the reaction time for the olefin isomerization process may be greater than 5 minutes; alternatively, greater than 15 minutes; alternatively greater than 30 minutes; or alternatively, greater than 45 minutes; or alternatively greater than 1 hour. In other embodiments, the reaction time for the olefin isomerization process may range from 5 minute to 96 hours; alternatively, range from 15 minutes to 72 hours; alternatively, range from 30 minutes to 36 hours; or alternatively, range from 45 minutes to 24 hours.

In an embodiment, the reactor pressure for the olefin isomerization process may be chosen by one of ordinary skill in the art to be compatible with the user desired processes and equipment. For example, the reaction pressure for the olefin isomerization process may be maintained at atmospheric pressure. In other embodiments, the reaction pressure for the olefin isomerization process may be maintained above atmospheric pressure. In further embodiments, the reaction pressure for the olefin isomerization process may range from atmospheric pressure to 3000 psig; alternatively, from atmospheric pressure to 2000 psig; or alternatively from atmospheric pressure to 1000 psig. In particular embodiments, the reaction pressure for the olefin isomerization process may be maintained at a pressure greater than or equal to a pressure that maintains the olefin in a liquid state at the reaction temperature employed. In some other embodiments, the reaction pressure for the olefin isomerization process may be maintained at a pressure ranging from a pressure that maintains the olefin in a liquid state at the reaction temperature employed to 3000, 2000, or 1000 psig.

In a non-limiting example, the process for isomerizing an olefin (e.g. an alpha olefin) utilizes a hexadentate bimetallic catalyst wherein the metal compounds comprise any cobalt described herein. In some embodiments, the cocatalyst of the olefin isomerization process comprises an organoaluminum compound; alternatively an organoaluminum halide; or alternatively, an alumoxane. Suitable organoaluminum compounds and organoaluminum halide compounds are described herein. Persons with ordinary skill in the art would recognize the organoaluminum compounds and organoaluminum halide compounds in the lists of suitable cocatalyst described herein. Non-limiting examples of suitable organoaluminum halide compounds which may be utilized as a cocatalyst for the olefin isomerization process include diethyl aluminum chloride; or alternatively, ethylaluminum dichloride. Non-limiting examples of suitable alumoxanes which may be utilized as a cocatalyst for the olefin isomerization process include methylalumoxane; or alternatively, modified methylalumoxane. In some non-limiting examples, the isomerization process utilizes a metal of the cocatalyst to the metal of the hexadentate bimetallic catalyst ratio ranging from 1:1 to 300:1; alternatively, ranging from 3:1 to 200:1; or alternatively, ranging from 5:1 to 100:1.

In an embodiment, the dimerization or isomerization of an olefin may be carried out as a batch process. The dimerization may be carried out by contacting the catalyst or catalyst system with one or more olefin monomers as described herein. In other embodiments, the dimerization may be carried out by activating the catalyst in the presence of a suitable cocatalyst and/or solvent, and contacting the activated complex with one or more monomers. The dimerization may be carried out under suitable reaction conditions described herein to dimerize the olefin monomer. The dimer product may comprise linear internal dimers as described herein.

In an embodiment, the dimerization or isomerization may be a carried out as a continuous process employing one or more reactors and the reagents described herein. For example, the reactor may comprise a loop reactor, tubular reactor, continuous stirred tank reactor (CSTR), or combinations thereof.

In various embodiments, the continuous reactor may be employed in the form of different types of reactors in combination, and in various arrangements. In an embodiment, the continuous reactor may be a combination of a tubular reactor and a CSTR. In other embodiments, the continuous reactor may be employed as reactors in series, reactors in parallel, or combinations thereof. In an embodiment, the continuous reactor may be more than one CSTR in series. In another embodiment, the continuous reactor may be a tubular reactor and a loop reactor in series.

In alternative embodiments, a dimers or isomerized olefin products described herein may be further converted to alcohols; alternatively, is further converted to a polyalphaolefin, a poly polyinternalolefin, or combinations thereof; alternatively, is further converted to a carboxylic acid; alternatively, is further converted to a linear alkyl benzene; alternatively, is further converted to a functional drilling fluid; alternatively, is further converted to an alkyl succinic anhydride; alternatively, is further converted to an olefin sulfonate; alternatively, is further converted to an alkane sulfonate; alternatively, is further converted to an epoxide; alternatively, is used as comonomer for production of polyethylene; alternatively, undergoes a purification process such that the weight percent of one or more of the dimers therein is increased; and combinations thereof, such processes being carried out as would be known to one of skill in the relevant art.

The dimer olefin or isomerized olefin products made herein may be further polymerized with other olefins to form polyolefins. They may also be homopolymerized. These polymers may be made by a number of known methods, such as Ziegler-Natta-type polymerization, metallocene catalyzed polymerization, and other methods, see for instance World Patent Application 96/23010; see for instance Angew. Chem., Int. Ed. Engl., vol. 34, p. 1143-1170 (1995), European Patent Application 416,815 and U.S. Pat. No. 5,198,401 for information about metallocene-type catalysts, and J. Boor Jr., Ziegler-Natta Catalysts and Polymerizations, Academic Press, New York, 1979 and G. Allen, et al., Ed., Comprehensive Polymer Science, Vol. 4, Pergamon Press, Oxford, 1989, p. 1-108, 409-412 and 533-584, for information about Ziegler-Natta-type catalysts, and H. Mark, et al., Ed., Encyclopedia of Polymer Science and Engineering, Vol. 6, John Wiley & Sons, New York, 1992, p. 383-522, for information about polyethylenes, and all of these references are herein incorporated by reference.

EXAMPLES

The invention having been generally described, the following examples are given as particular embodiments of the invention and to demonstrate the practice and advantages thereof. It is understood that the examples are given by way of illustration and are not intended to limit the specification or the claims in any manner.

Example 1

A HBC was prepared as shown in Scheme 1.

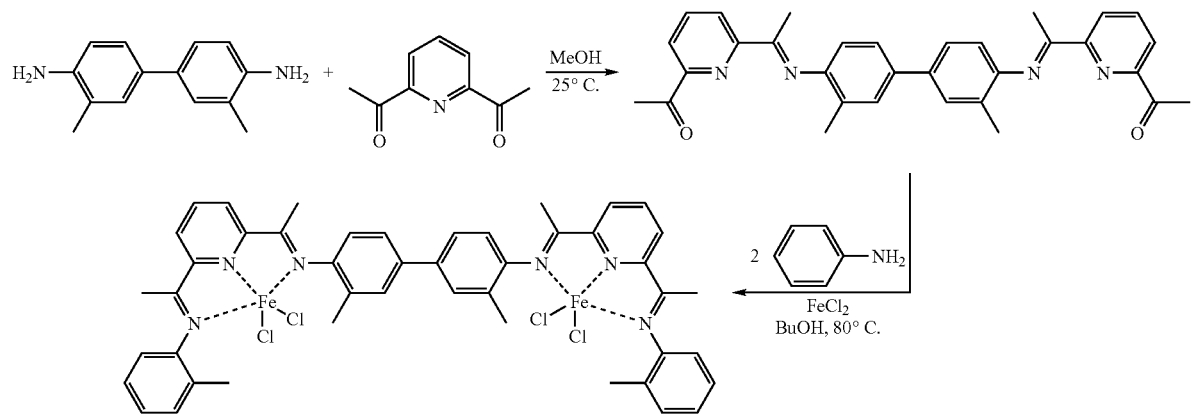

HBC 11

Specifically, 2-diacetylpyridine (DAP), 5.0 g (30.9 mmol), was dissolved in 75 ml of methanol (MeOH) with 0.3 ml of formic acid in a two-necked flask. o-tolidine, 2.17 g (10.2 mmol), was dissolved in 75 ml of MeOH in a separate flask and poured into an addition funnel. The contents of the addition funnel were added to the two-necked flask over the course of 12 hours at 25° C., with pressure relief of the flask to a bubbler connected to the other neck of the flask. Within the first hour, solid material began to precipitate. After completion of the addition, the reaction was allowed to stir for two additional days before a yellow solid was isolated and washed with MeOH until the MeOH washes became virtually colorless. A product having the molecular formula $C_{22}H_{30}N_4O_2$, a molecular weight of 502 g/mol and a yield of 95% corresponding to 4.90 g was obtained which is consistent with the formation of the hexadentate diketone. $^1$H NMR (300 MHz, CDCl$_3$): δ=8.38, d, 2H; 8.17, d, 2H; 7.97, t, 2H; 7.58, s, 2H; 7.50, d, 2H; 6.81, d, 2H; 2.80, s, 6H; 2.40, s, 6H; 2.21, s, 6H.

1.0 g (1.99 mmol) of the hexadentate diketone was transferred to a 30 ml vial containing a stirbar and 531 mg (4.18 mmol) of FeCl$_2$ was added to the hexadentate diketone in a drybox. In a separate vial 639 mg (5.97 mmol) of o-toluidine was dissolved in 12 ml of anhydrous n-butanol. The solution of o-toluidine was transferred to the vial containing the hexadentate ligand and FeCl$_2$ and the vial was sealed and left to stir overnight at 80° C. After being allowed to react for 14 hours the reaction was cooled to room temperature, the contents of the vial filtered in a drybox and the solids washed with ethanol and dried to yield 1.715 g (92%) of the hexadentate bimetallic catalyst. Anal. Calc. (Found) for $C_{32}H_{30}N_4O$: C, 59.13 (59.02); H, 4.75 (5.15); N, 8.99 (8.68).

The hexadentate bimetallic catalyst having Structure HBC 11 was prepared as described herein. 1-decene and 1-decene were obtained from Chevron Phillips Chemical Company, LP and dried over molecular sieves prior to use. Modified methyl alumoxane-3A in n-heptane was obtained from Akzo and used as is.

A two liter Zipperclave™ reactor was heated under vacuum at 50° C. for several hours. The reactor was cooled to room temperature under nitrogen. The Zipperclave™ reactor was opened and a sealed NMR tube containing 50 mg of HBC 1 was attached to the stirrer shaft of the Zipperclave™. The Zipperclave™ reactor was resealed and placed under vacuum. A mixture containing 400 grams of 1-decene, 400 grams of 1-dodecene, and 8.6 ml of a MMAO-3A solution (7 weight percent aluminum) was charged to the Zipperclave™ under vacuum. The reaction Zipperclave™ stirrer was started to break the NMR tube containing HBC 11 and the reaction was initiated and allowed to proceed overnight. The starting temperature of the reaction was 23° while the maximum temperature attained during the reaction was 31° C.

Upon reaction completion, the Zipperclave™ was opened. The reactor contents were washed with aqueous sodium hydroxide. The organic layer was then dried and the 1-decene and 1-dodecene were removed by rotary evaporation under reduced pressure. The olefin dimerization produced 513 grams of olefin oligomers (64.1 weight percent conversion of olefin monomer). The olefin oligomers were analyzed by gas chromatography. The olefin oligomers contained 77.4 weight percent dimers, 22.2 weight percent trimers, and 0.4 weight percent tetramers. The dimer fraction contained approximately 75.4 weight percent linear dimers.

Without further elaboration, it is believed that one skilled in the art can, using the description herein, utilize the present invention to its fullest extent. While preferred inventive aspects have been shown and described, modifications thereof can be made by one skilled in the art without departing from the spirit and teachings of the invention. The embodiments and examples described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, has, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The disclosures of all patents, patent applications, and publications cited herein are hereby incorporated by reference, to the extent that they provide exemplary, procedural or other details supplementary to those set forth herein.

What is claimed is:

1. A process for dimerizing alpha olefins comprising:
  a) contacting (i) an alpha olefin having at least 3 carbon atoms, (ii) a hexadentate bimetallic catalyst, and (iii) a cocatalyst, wherein the hexadentate bimetallic complex has the following structure,

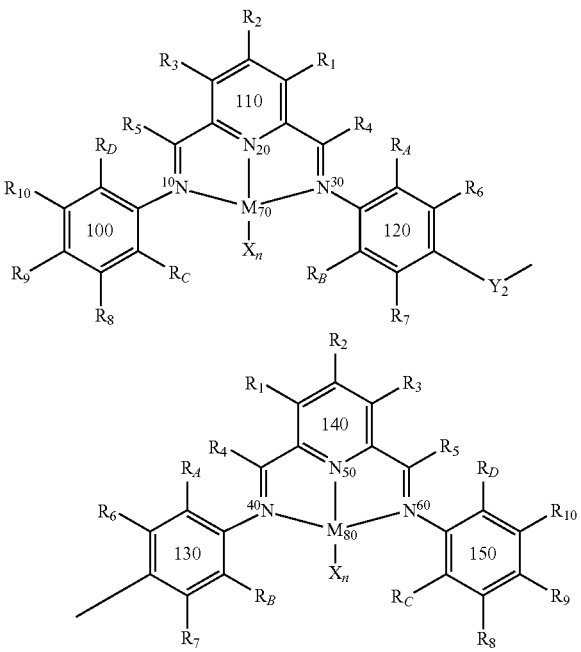

and wherein
  $R_1$, $R_2$, and $R_3$ are hydrogen;
  $R_4$ and $R_5$ are each independently an alkyl group;

$R_6$, $R_7$, $R_8$, $R_9$, and $R_{10}$ are each hydrogen;

$R_A$, $R_B$, $R_C$, and $R_D$ are each independently an alkyl group;

$Y_2$ is a bond or an alkylene group having from 1 to 10 carbon atoms; and $MX_n$ represents a metal compound where M is iron, X is a halide or acetonate; and n is 2 or 3; and b) dimerizing the alpha olefin in a reaction zone at conditions effective to dimerize an alpha olefin to form a reaction zone effluent comprising alpha olefin oligomers including alpha olefin dimers, wherein greater than 40 weight percent of the alpha olefin has been converted to alpha olefin oligomers and the alpha olefin oligomers comprise greater than 75 weight percent alpha olefin dimers.

2. The process of claim 1, wherein the alpha olefin dimers comprise greater than 60 weight percent linear alpha olefin dimers.

3. The process of claim 1, wherein the alpha olefin dimers comprise from 10 to 40 weight percent methyl branched alpha olefin dimers wherein the methyl branch is on a carbon atom positioned one or two carbon atoms away from the carbon-carbon double bond.

4. The process of claim 1, wherein the cocatalyst comprises one or more alumoxanes.

5. The process of claim 1, wherein the molar ratio of the metal of the cocatalyst to the metal of the hexadentate bimetallic complex ranges from 10:1 to 3,000:1.

6. The process of claim 1, wherein the alpha olefin has at least 5 carbon atoms and comprises greater than 90 mole percent linear alpha olefins.

7. The process of claim 1, wherein the alpha olefin has at least 5 carbon atoms and consists essentially of a normal alpha olefin.

8. The process of claim 1, wherein the alpha olefin has at least 4 carbon atoms and consists essentially of normal alpha olefin; from 60 to 90 weight percent of the normal alpha olefin dimers are linear; and the normal alpha olefin dimers comprise from 10 to 40 weight percent methyl branched normal alpha olefin dimers.

9. A process for dimerizing olefins comprising:
a) contacting (i) an alpha olefin having at least 3 carbon atoms, (ii) a hexadentate bimetallic complex comprising a cobalt compound, and (iii) a cocatalyst, wherein the hexadentate bimetallic complex has the following structure,

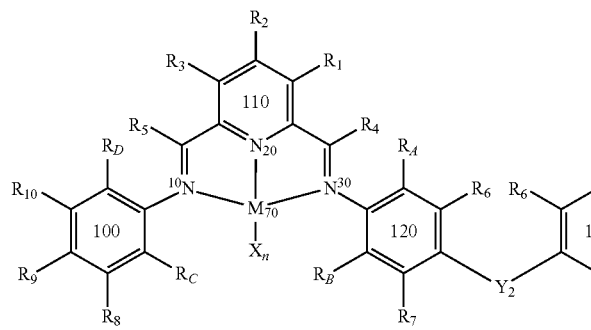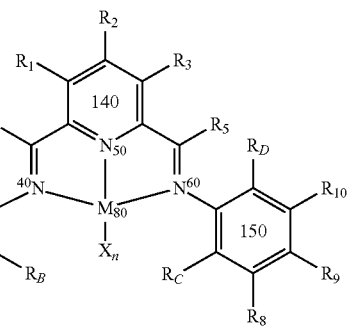

and wherein
$R_1$, $R_2$, and $R_3$ are hydrogen;
$R_4$ and $R_5$ are each independently an alkyl group;
$R_6$, $R_7$, $R_8$, $R_9$, and $R_{10}$ are each hydrogen;
$R_A$, $R_B$, $R_C$, and $R_D$ are each independently an alkyl group;

$Y_2$ is a bond or an alkylene group having from 1 to 10 carbon atoms; and $MX_n$ represents a metal compound where M is iron, X is a halide or acetonate; and n is 2 or 3; and b) dimerizing the alpha olefin in a reaction zone at conditions effective to dimerize the alpha olefin to form a reaction zone effluent comprising oligomers including dimers;

wherein greater than 20 weight percent of the alpha olefin has been converted to oligomers, greater than 30 weight percent of the oligomers are dimers, and greater than 85 mole percent of the dimers are linear.

10. The process of claim 9, wherein the cocatalyst comprises one or more alumoxanes.

11. The process of claim 9, wherein the molar ratio of the metal of the cocatalyst to the metal of the hexadentate bimetallic complex ranges from 10:1 to 3,000:1.

12. The process of claim 10, wherein the molar ratio of the metal of the cocatalyst to the metal of the hexadentate bimetallic complex ranges from 10:1 to 3,000:1.

13. The process of claim 9, wherein greater than 40 weight percent of the alpha olefin has been converted to alpha olefin oligomers and the alpha olefin oligomers comprise greater than 50 weight percent alpha olefin dimers.

14. The process of claim 13, wherein the alpha olefin dimers comprise greater than 90 weight percent linear alpha olefin dimers.

15. The process of claim 13, wherein the alpha olefin dimers comprise greater than 95 weight percent linear alpha olefin dimers.

16. The process of claim 9, wherein 40 to 80 weight percent of the alpha olefin has been converted to alpha olefin oligomers; the alpha olefin oligomers comprise from 50 to 85 weight percent alpha olefin dimers; and the alpha olefin dimers comprise from 90 to 99.9 weight percent linear alpha olefin dimers.

17. The process of claim 1, wherein the alpha olefin has at least 4 carbon atoms and comprises greater than 75 mole percent normal alpha olefin; from 60 to 90 weight percent of the alpha olefin dimers are linear; and the alpha olefin dimers comprise from 10 to 40 weight percent methyl branched alpha olefin dimers.

18. The process of claim 4, wherein the alpha olefin dimers comprise greater than 60 weight percent linear alpha olefin dimers.

19. The process of claim 4, wherein the alpha olefin dimers comprise from 10 to 40 weight percent methyl branched alpha olefin dimers wherein the methyl branch is on a carbon atom positioned one or two carbon atoms away from the carbon-carbon double bond.

20. The process of claim 5, wherein the alpha olefin dimers comprise greater than 60 weight percent linear alpha olefin dimers.

21. The process of claim 5, wherein the alpha olefin dimers comprise from 10 to 40 weight percent methyl branched alpha olefin dimers wherein the methyl branch is on a carbon atom positioned one or two carbon atoms away from the carbon-carbon double bond.

22. The process of claim 4, wherein the alpha olefin has at least 5 carbon atoms and comprises greater than 90 mole percent linear alpha olefins.

23. The process of claim 4, wherein the alpha olefin has at least 5 carbon atoms and consists essentially of a normal alpha olefin.

24. The process of claim 5, wherein the alpha olefin has at least 5 carbon atoms and comprises greater than 90 mole percent linear alpha olefins.

25. The process of claim 5, wherein the alpha olefin has at least 5 carbon atoms and consists essentially of a normal alpha olefin.

26. The process of claim 10, wherein greater than 40 weight percent of the alpha olefin has been converted to alpha olefin oligomers and the alpha olefin oligomers comprise greater than 50 weight percent alpha olefin dimers.

* * * * *